(12) United States Patent
Keana et al.

(10) Patent No.: US 6,949,516 B2
(45) Date of Patent: *Sep. 27, 2005

(54) DIPEPTIDE APOPTOSIS INHIBITORS AND THE USE THEREOF

(75) Inventors: John F. W. Keana, Eugene, OR (US); Sui Xiong Cai, San Diego, CA (US); John Guastella, Irvine, CA (US); Wu Yang, Irvine, CA (US); John A. Drewe, Costa Mesa, CA (US); Eckard Weber, San Diego, CA (US)

(73) Assignee: Cytovia, Inc., San Diego, CA (US)

( * ) Notice: Subject to any disclaimer, the term of this patent is extended or adjusted under 35 U.S.C. 154(b) by 10 days.

This patent is subject to a terminal disclaimer.

(21) Appl. No.: 10/429,095

(22) Filed: May 5, 2003

(65) Prior Publication Data

US 2003/0181391 A1 Sep. 25, 2003

Related U.S. Application Data

(60) Division of application No. 09/653,279, filed on Aug. 31, 2000, now Pat. No. 6,596,693, which is a division of application No. 09/270,736, filed on Mar. 16, 1999, now Pat. No. 6,184,210, which is a continuation-in-part of application No. 09/168,945, filed on Oct. 9, 1998, now abandoned.

(60) Provisional application No. 60/061,676, filed on Oct. 10, 1997.

(51) Int. Cl.[7] .......................... A61K 38/04; C07K 5/04; C07C 233/45

(52) U.S. Cl. ........................ 514/19; 514/885; 560/169; 560/171

(58) Field of Search .................... 514/19, 885; 560/169, 560/171

(56) References Cited

U.S. PATENT DOCUMENTS

| | | | |
|---|---|---|---|
| 4,153,688 A | 5/1979 | Dimicoli et al. | |
| 4,518,528 A | 5/1985 | Rasnick | |
| 5,416,013 A | 5/1995 | Black et al. | |
| 5,430,128 A | 7/1995 | Chapman et al. | |
| 5,434,248 A | 7/1995 | Chapman et al. | |
| 5,462,939 A | 10/1995 | Dolle et al. | |
| 5,585,357 A | 12/1996 | Dolle et al. | |
| 5,677,283 A | 10/1997 | Dolle et al. | |
| 5,756,465 A | 5/1998 | Sleath et al. | |
| 5,843,904 A | 12/1998 | Bemis et al. | |
| 5,866,545 A | 2/1999 | Hagmann et al. | |
| 5,869,519 A | 2/1999 | Karanewsky et al. | |
| 5,877,197 A | 3/1999 | Karanewsky et al. | |
| 5,932,549 A | 8/1999 | Allen et al. | |
| 6,136,787 A | 10/2000 | Black et al. | |
| 6,153,591 A | 11/2000 | Cai et al. | |
| 6,184,244 B1 | 2/2001 | Karanewsky et al. | |
| 6,197,750 B1 | 3/2001 | Karanewsky et al. | |
| 6,242,422 B1 | 6/2001 | Karanewsky et al. | |
| 6,355,618 B1 | 3/2002 | Cai et al. | |
| 6,495,522 B1 | 12/2002 | Wang et al. | |
| 6,515,173 B1 | 2/2003 | Ternansky et al. | |
| 6,525,024 B1 | 2/2003 | Ternansky et al. | |
| 6,544,951 B2 | 4/2003 | Karanewsky et al. | |
| 6,566,338 B1 | 5/2003 | Weber et al. | |
| 6,573,259 B2 * | 6/2003 | Golec et al. | ................. 514/221 |
| 2002/0042376 A1 | 4/2002 | Karanewsky et al. | |
| 2002/0137686 A1 | 9/2002 | Ternansky et al. | |
| 2003/0232788 A1 | 12/2003 | Karanewsky et al. | |

FOREIGN PATENT DOCUMENTS

| | | |
|---|---|---|
| EP | 0 519 748 A2 | 12/1992 |
| EP | 0 618 223 A2 | 10/1994 |
| WO | WO 91/15577 | 10/1991 |
| WO | WO 93/05071 | 3/1993 |
| WO | WO 96/03982 | 2/1996 |
| WO | WO 96/20721 | 7/1996 |
| WO | WO 98/10778 | 3/1998 |
| WO | WO 98/11109 | 3/1998 |
| WO | WO 98/41232 | 9/1998 |
| WO | WO 99/18781 | 4/1999 |
| WO | WO 99/47154 | 9/1999 |

OTHER PUBLICATIONS

Alnemri, E.S. et al., "Human ICE/CED–3 Protease Nomenclature," *Cell* 87:171, Cell Press, Cambridge, MA (1996).

An, S., and Knox, K.A., "Ligation of CD40 rescues Ramos–Burkitt lymphoma B cells from calcium ionophore– and antigen receptor–triggered apoptosis by inhibiting activation of the cysteine protease CPP32/Yama and cleavage of its substrate PARP," *FEBS Lett.* 386:115–122, Elsevier Science Publishers B.V., Amsterdam (1996).

Angliker, H., et al., "The synthesis of lysylfluoromethanes and their properties as inhibitors of trypsin, plasmin and cathepsin B," *Biochem. J.* 241:871–875, The Biochemical Society, London, England (1987).

(Continued)

*Primary Examiner*—Bennett Celsa
(74) *Attorney, Agent, or Firm*—Sterne, Kessler, Goldstein & Fox P.L.L.C.

(57) ABSTRACT

The present invention is directed to novel dipeptides thereof, represented by the general Formula I:

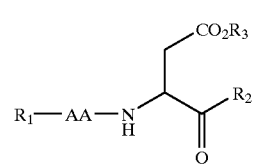

where $R_1$–$R_3$ and AA are defined herein. The present invention relates to the discovery that compounds having Formula I are potent inhibitors of apoptotic cell death. Therefore, the inhibitors of this invention can retard or block cell death in a variety of clinical conditions in which the loss of cells, tissues or entire organs occurs.

14 Claims, 11 Drawing Sheets

OTHER PUBLICATIONS

Black, R.A. et al., A Pre–aspartate–specific Protease from Human Leukocytes That Cleaves Pro–interleukin–2α, *J. Biol. Chem.* 264:5323–5326, The American Society for Biochemistry and Molecular Biology, Baltimore, MD (1989).

Black, S.C. et al., "Co–localization of the Cysteine Protease Caspase–3 with Apoptotic Myocytes after In Vivo Myocardial Ischemia and Reperfusion in the Rat," *J. Mol. Cell. Cardiol.* 30:733–742, Academic Press, Inc., New York, NY (Apr. 1998).

Bourne, E.J. et al., "Studies of Trifluoroacetic Acid. Part XVIII. Reaction of N–Aroylglycines with Perfluoro–carboxylic Anhydrides." *J. Chem. Soc. Part II*:1771–1775, The Chemical Society, London, England (1961).

Conaldi, P.G. et al., "HIV–1 Kills Renal Tubular Epithelial Cells In Vitro by Triggering an Apoptotic Pathway Involving Caspase Activation and Fas Upregulation," *J. Clin. Invest.* 102:2041–2049, The American Society for Clinical Investigation, Inc., New York, NY (Dec. 1998).

del Pozo, O., and Lam, E., "Caspases and programmed cell death in the hypersensitive response of plants to pathogens," *Curr. Biol.* 8:1129–1132, Current Biology Ltd., London, England (Oct. 1998).

di Giovine, F.S., and Duff, G.W., "Interleukin 1: the first interleukin," *Immunology Today* 11:13–14, Elsevier Science Publishers Ltd., Barking, England (1990).

Dinarello, C. A., "Interleukin–1 and Interleukin–1 Antagonism," *Blood* 77:1627–1652, American Society for Hematology, Philadelphia, PA (1991).

Dolle, R.E. et al., "$P_1$ Aspartate–Based Peptide α–((2, 6–Dichlorobenzoyl)oxy)methyl Ketones as Potent Time–Dependent Inhibitors of Interleukin–1β–Converting Enzyme," *J. Med. Chem.* 37:563–564, American Chemical Society, Washington, DC (1994).

Dolle, R.E. et al., "Aspartyl α–((1–Phenyl–3–(trifluoromethyl)–pyrazol–5–yl)oxy)methyl Ketones as Interleukin–1β Converting Enzyme Inhibitors. Significance of the $P_1$ and $P_3$ Amido Nitrogens for Enzyme–Peptide Inhibitor Binding," *J. Med. Chem.* 37:3863–3866, American Chemical Society, Washington, DC (1994).

Dolle, R.E. et al., "Aspartyl α–((Diphenylphosphinyl)oxy)methyl Ketones as Novel Inhibitors of Interleukin–1β Converting Enzyme. Utility of the Diphenylphosphinic Acid Leaving Group for the Inhibition of Cysteine Proteases," *J. Med. Chem.* 38:220–222, American Chemical Society, Washington, DC (1995).

Ellis, R.E. et al., "Mechanisms and Functions of Cell Death," *Ann. Rev. Cell Biol.* 7:663–698, Annual Reviews, Palo Alto, CA (1991).

Emery, E. et al., "Apoptosis after traumatic human spinal cord injury,"*J. Neurosurg.* 89:911–920, American Association of Neurological Surgeons, Charlottesville, VA (Dec. 1998).

Goldberg, Y.P. et al., "Cleavage of huntingtin by apopain, a proapoptotic cysteine protease, is modulated by the polyglutamine tract," *Nature Genetics* 13:442–449, Nature Publishing Co., New York, NY (1996).

Graybill, T.L. et al., "α–((Tetronoyl)oxy)– and α–((Tetramoyl)oxy)methyl Ketone Inhibitors of the Interleukin–1β Converting Enzyme (ICE)," *Bioorg. Med. Chem. Lett.* 7:41–46, Elsevier Science Ltd., Oxford, England (1997).

Greenberg, J.T. et al., "Programmed Cell Death in Plants: A Pathogen–Triggered Response Activated Coordinately with Multiple Defense Functions," *Cell* 77:551–563, Cell Press, Cambridge, MA (1994).

Grobmyer, S.R. et al., "Peptidomimetic Fluoromethylketone Rescues Mice from Lethal Endotoxic Shock," *Mol. Med.* 5:585–594, Johns Hopkins University Press, Baltimore, MD (Sep. 1999).

Hara, H. et al., "Inhibition of interleukin 1β converting enzyme family proteases reduces ischemic and excitotoxic neuronal damage," *Proc. Natl. Acad. Sci. USA* 94:2007–2012, National Academy of Sciences, Washington, DC (Mar. 1997).

Hiraoka, J. et al., "Participation of apoptosis in renal amyloidosis," *Jpn. J. Nephrol.* 40:276–283, Japanese Society of Nephrology, Tokyo, Japan (May 1998).

Hotchkiss, R.S. et al., "Prevention of lymphocyte cell death in sepsis improves survival in mice," *Proc. Natl. Acad. Sci. USA* 96:14541–14546, National Academy of Sciences, Washington, DC (Dec. 1999).

Jaeschke, H. et al., "Activation of Caspase 3 (CPP32)–Like Proteases Is Essential for TNF–α–Induced Hepatic Parenchymal Cell Apoptosis and Neutrophil–Mediated Necrosis in a Murine Endotoxin Shock Model," *J. Immun.* 160:3480–3486, American Association of Immunologists, Baltimore, MD (Apr. 1998).

Jones, R.A. et al., "Fas–Mediated Apoptosis in Mouse Hepatocytes Involves the Processing and Activation of Caspases," *Hepatology* 27:1632–1642, American Association for the Study of Liver Diseases, Philadelphia, PA (Jun. 1998).

Kermer, P. et al., "Inhibition of CPP32–Like Proteases Rescues Axotomized Retinal Ganglion Cells from Secondary Cell Death In Vivo," *J. Neuroscience* 18:4656–4662, Society for Neuroscience, Washington, DC (Jun. 1998).

Kubo, S. et al., "Hepatocyte injury in tyrosinemia type 1 is induced by fumarylacetoacetate and is inhibited by caspase inhibitors," *Proc. Natl. Acad. Sci. USA* 95:9552–9557, National Academy of Sciences, Washington, DC (Aug. 1998).

Lepschy, J., "Acylierung von Oxazolinonen– (5) unter besonderer Berücksichtigung der Dakin–West–Reaktion trifunktioneller Aminosäuren," Ph.D. Thesis, Technischen Universität München (1971).

Lieberthal, W. et al., "Necrosis and Apoptosis in Acute Renal Failure," *Sem. Nephr.* 18:505–518, W.B. Saunders Company, Philadelphia, PA (Sep. 1998).

Lotem, J., and Sachs, L., "Differential suppression by protease inhibitors and cytokines of apoptosis induced by wild–type p53 and cytotoxic agents," *Proc. Natl. Acad. Sci. USA* 93:12507–12512, National Academy of Sciences, Washington, DC (1996).

Mattson, M.P. et al., "Amyloid β–peptide induces apoptosis–related events in synapses and dendrites," *Brain Res.* 807:167–176, Elsevier Science B.V., Amsterdam, Netherlands (Oct. 1998).

Maulik, N. et al., "Oxidative Stress Developed During the Reperfusion of Ischemic Myocardium Induces Apoptosis," *Free Rad. Biol. & Med.* 24:869–875, Elsevier Science Inc., Tarrytown, NY (Mar. 1998).

Miller, P.E. et al., "Photoreceptor cell death by apoptosis in dogs with sudden acquired retinal degeneration syndrome," *Am. J. Vet. Res.* 59:149–152, American Veterinary Medical Association, Schaumburg, IL (Feb. 1998).

Miura, M. et al., "Induction of Apoptosis in Fibroblasts in Fibroblasts by IL–1β–Converting Enzyme, a Mammalian Homolog of the C. elegans Cell Death Gene ced–3," Cell 75:653–660, Cell Press, Cambridge, MA (1993).

Mjalli, A.M.M. et al., "Phenylalkyl Ketones as Potent Reversible Inhibitors of Interleukin–1β Converting Enzyme," Bioorg. Med. Chem. Lett. 3:2689–2692, Elsevier Science Ltd., Oxford, England (1993).

Mjalli, A.M.M. et al., "Activated Ketones as Potent Reversible Inhibitors of Interleukin–1β Converting Enzymes," Bioorg. Med. Chem. Lett. 4:1965–1968, Elsevier Science Ltd., Oxford, England (1994).

Mjalli, A.M.M. et al., "Inhibition of Interleukin–1β Converting Enzyme by N–Acyl–aspartic Acid Ketones," Bioorg. Med. Chem. Lett. 5:1405–1408 Elsevier Science Ltd., Oxford, England (1995).

Mjalli, A.M.M. et al., "Inhibition of Interleukin–1β Converting Enzyme by N–Acyl–aspartyl Aryloxymethyl Ketones," Bioorg. Med. Chem. Lett. 5:1409–1414, Elsevier Science Ltd., Oxford, England (1995).

Mosley, B. et al., "The Interleukin–1 Receptor Binds the Human Interleukin–1α Precursor but Not the Interleukin–1β Precursor," J. Biol. Chem. 262:2941–2944, American Society of Biological Chemists, Inc., Baltimore, MD (1987).

Mundle, S. D. et al., "Evidence for Involvement of Tumor Necrosis Factor–α in Apoptotic Death of Bone Marrow Cells in Myelodysplastic Syndromes," Am. J. Hemat. 60:36–47, Wiley–Liss, Inc., New York, NY (Jan. 1999).

Oppenheim, J. J. et al., "There is more than one interleukin 1," Immun. Today 7:45–56, Elsevier Science Publishers B.V., Amsterdam, Netherlands (1986).

Orrenius, S., "Apoptosis: molecular mechanisms and implications for human disease," J. Internal Medicine 237:529–536, Blackwell Science Ltd., Oxford, England (1995).

Ortiz, A. et al., "Cyclosporine A induces apoptosis in murine tubular epithelial cells: Role of caspases." Kidney Int'l. 54:S–25–S–29, International Society of Nephrology, Amsterdam, Netherlands (Dec. 1998).

Peleg, S. et al, "1,25–Dihydroxyvitamin $D_3$ and its analogs inhibit acute myelogenous leukemia progenitor proliferation by suppressing interleukin–1β production," Chemical Abstracts 127, Abstract No. 315124p, American Chemical Society, Washington, DC (1997).

Rasnick, D., "Synthesis of Peptide Fluoromethyl Ketones and the Inhibition of Human Cathepsin B," Anal. Biochem. 149:461–465, Academic Press, New York, NY (1985).

Rauber, P. et al., "The synthesis of peptidylfluoromethanes and their properties as inhibitors of serine proteinases and cysteine proteinases," Biochem. J. 239:633–640, The Biochemical Society, London, England (1986).

Revesz, L. et al., "Synthesis of P1 Aspartate–Based Peptide Acyloxymethyl and Fluoromethyl Ketones as Inhibitors of Interleukin–1β–Converting Enzyme," Tet. Lett. 35:9693–9696, Elsevier Science Ltd., United Kingdom (1994).

Rich, D.H., "Inhibitors of aspartic proteinases," in Proteinase inhibitors. Research monographs in cell and tissue physiology. vol. 12, Barrett, A.J. and G. Salvesen, eds., Elsevier, Amsterdam, Holland, pp. 179–208 (1986).

Richberg, M.H. et al., "Dead cells do tell tales," Curr. Op. Plant Bio. 1:480–485, Elsevier Science Ltd., United Kingdom (Dec. 1998).

Rodriguez, I. et al., "Systemic Injection of a Tripeptide Inhibits the Intracellular Activation of CPP32–like Proteases In Vivo and Fully Protects Mice against Fas–mediated Fulminant Liver Destruction and Death," J. Exp. Med. 184:2067–2072, The Rockefeller University Press, New York, NY (1996).

Shaw, E. et al., "Peptidyl fluoromethyl ketones as thiol protease inhibitors," Biomed. Biochim. Acta 45:1397–1403, Academie Verlag, Berlin, Germany (1986).

Sample, G. et al., "Peptidomimetic Aminomethylene Ketone Inhibitors of Interleukin–1β–Converting Enzyme (ICE)," Bioorg. Med. Chem. Lett. 8:959–964, Elsevier Science Ltd., Oxford, England (1998).

Sheikh, M.S. et al., "Ultraviolet–irradiation–induced apoptosis is mediated via ligand independent activation of tumor necrosis factor receptor 1," Oncogene 17:2555–2563, Stockton Press, London, England (Nov. 1998).

Sleath, P.R. et al., "Substrate Specificity of the Protease That Pocesses Human Interleukin–1β," J. Biol. Chem. 265:14526–14528, American Society for Biochemistry and Moledular Biology, Inc., Baltimore, MD (1990).

Slomiany, B.L. et al., "Activation of Apoptotic Caspase–3 and Nitric Oxide Synthase–2 in Buccal Mucosa with Chronic Alcohol Ingestion," Biochem. & Mol. Bio. Int'l. 45:1199–1209, Academic Press, Sydney, Australia (Sep. 1998).

Steinberg, D., "Caspase Inhibitors. Molecules Sought For Treatment of Diverse Disorders," Gen. Eng. News 18:16, 38,51, Mary Ann Liebert, Inc., New York, NY (Jul. 1998).

Suzuki, A., "The Dominant Role of CPP32 Subfamily in Fas–Mediated Hepatitis," Proc. Soc. Exp. Biol. Med. 217:450–454, Society for Experimental Biology and Medicine, Cambridge, MA (Apr. 1998).

Thornberry, N.A. et al., "A novel heterodimeric cysteine protease is required for interleukin–1β processing in monocytes," Nature 356:786–774, Nature Publishing Group, London, England (1992).

Thornberry, N.A. et al., "A Combinatorial Approach Defines Specificities of Members of the Caspase Family and Granzyme B," J. Biol. Chem. 272:17907–17911, American Society for Biochemistry and Molecular Biology, Inc., Baltimore, MD (1997).

Thornberry, N.A., "Caspases: key mediators of apoptosis," Chem. Biol. 5:R97–R103, Current Biology Ltd., London, England (May 1998).

Thornberry, N.A. et al., "Inactivation of Interleukin–1β Converting Enzyme by Peptide (Acyloxy)methyl Ketones," Biochemistry 33:3934–3940, American Chemical Society, Washington, DC (1994).

Wataya, Y. et al., "Cytotoxic mechanism of 1–(3–C–ethynyl–β–D–ribo–pentofuranosyl)cytosine (ECyd)," Chemical Abstracts 132, Abstract No. 273983p, American Chemical Society, Washington, DC (May 2000).

Weil, M. et al., "Is programmed cell death required for neural tube closure?" Curr. Biol. 7:281–284, Current Biology Ltd., London, England (1997).

Wyllie, A.H. et al., "Cell Death: The Significance of Apoptosis," Int. Rev. Cyt. 68:251–306, Academic Press, Inc., New York, NY (1980).

Wyllie, A.H., "Cell death: a new classification separating apoptosis from necrosis," in Cell Death in Biology and Pathology, Bowen and Lockin, eds., Chapman and Hall, New York, NY, pp. 9–34 (1981).

Xue, D. et al., "The Time Course for Infarction in a Rat Model of Transient Focal Ischemia," *Stroke 21*:166, Abstract No. 36, American Heart Association, Baltimore, MD (1990).

Yuan, J. et al., "The *C. elegans* Cell Death Gene ced–3 Encodes a Protein Similar to Mammalian Interleukin–1β–Converting Enzyme," *Cell* 75:641–652, Cell Press, Inc., Cambridge, MA (1993).

Cai, S.X. et al., U.S. Appl. No. 09/527,225, filed Mar. 16, 2000.

Jaeschke, Hartmut et al., "Protection against TNF–Induced Liver Parenchymal Cell Apoptosis during Endotoxemia by a Novel Caspase Inhibitor in Mice," *Toxicology and Applied Pharmacology 169*: 77–83, Academic Press, Inc., New York, NY (2000).

Russel, J.E., Office Communication for U.S. Appl. No. 09/270,735, 12 pages, United States Patent and Trademark Office (mailed Nov. 30, 1999).

Esmond, R.W., Applicant's Amendments to the Claims for U.S. Appl. No. 09/270,735, 11 pages, "Amendment and Reply Under 37 C.F.R. § 1.111" (filed Feb. 29, 2000).

Russel, J.E., Office Communication for U.S. Appl. No. 09/649,810, 6 pages, United States Patent and Trademark Office (mailed Dec. 7, 2001).

Chalker, B.E., Applicant's Amendments to the Claims for U.S. Appl. No. 09/649,810, 34 pages, "Amendment and Reply Under 37 C.F.R. § 1.111" (filed Apr. 5, 2002).

Supplementary Partial European Search Report, Application No. EP 98952166, European Patent Office, Netherlands, completed Oct. 4, 2004.

* cited by examiner

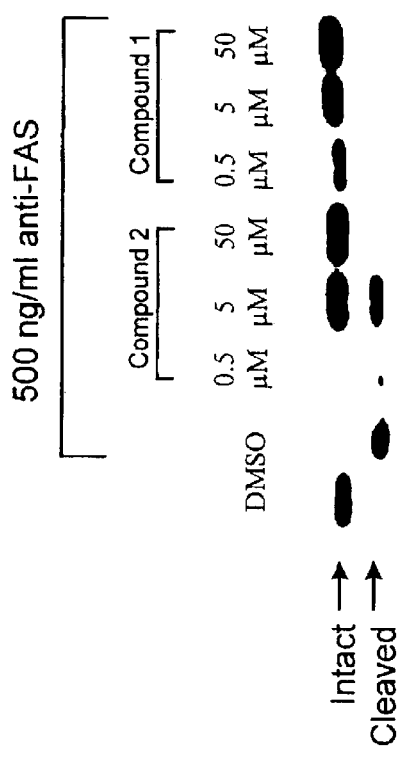
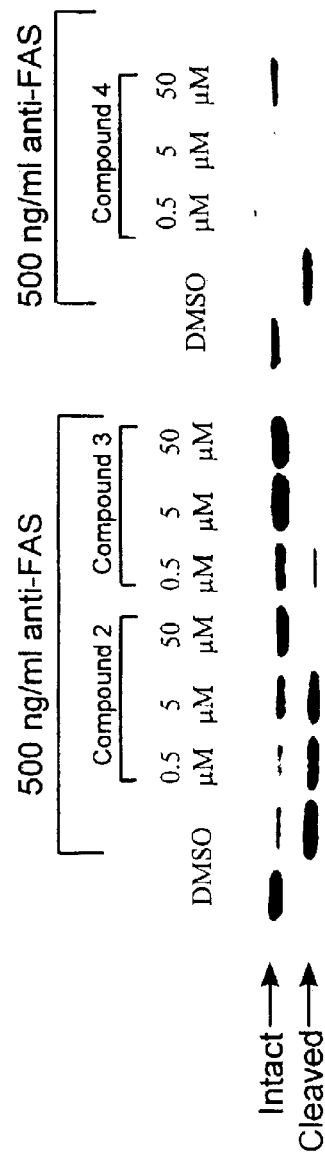
FIG. 7A
FIG. 7B
FIG. 7C

DIPEPTIDE APOPTOSIS INHIBITORS AND THE USE THEREOF

CROSS-REFERENCE TO RELATED APPLICATIONS

This application is a division of application Ser. No. 09/653,279, filed Aug. 31, 2000 now U.S. Pat. No. 6,596,693, which is a division of application Ser. No. 09/270,736, filed Mar. 16, 1999, now U.S. Pat. No. 6,184,210, which is a continuation-in-part of application Ser. No. 09/168,945, filed Oct. 9, 1998, abandoned, which claims the benefit of U.S. Provisional Application No. 60/061,676, filed Oct. 10, 1997, abandoned.

BACKGROUND OF THE INVENTION

1. Field of the Invention

This invention is in the field of medicinal chemistry. In particular, the invention relates to dipeptides which are potent inhibitors of apoptosis. The invention also relates to the use of these dipeptides for reducing or treating apoptotic cell death.

2. Description of Background Art

Organisms eliminate unwanted cells by a process variously known as regulated cell death, programmed cell death or apoptosis. Such cell death occurs as a normal aspect of animal development as well as in tissue homeostasis and aging (Glucksmann, A., *Biol. Rev. Cambridge Philos. Soc.* 26:59–86 (1951); Glucksmann, A., *Archives de Biologie* 76:419–437 (1965); Ellis et al., *Dev.* 112:591–603 (1991); Vaux et al., *Cell* 76:777–779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237:529–536 (1995)).

Apoptosis is achieved through an endogenous mechanism of cellular suicide (Wyllie, A. H., in *Cell Death in Biology and Pathology*, Bowen Lockshin, eds., Chapman and Hall (1981), pp. 9–34). A cell activates its internally encoded suicide program as a result of either internal or external signals. The suicide program is executed through the activation of a carefully regulated genetic program (Wylie et al., *Int. Rev. Cyt.* 68: 251 (1980); Ellis et al., *Ann. Rev. Cell Bio.* 7: 663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529–536 (1995)).

Mammalian interleukin-1β (IL-1β) plays an important role in various pathologic processes, including chronic and acute inflammation and autoimmune diseases (Oppenheim, J. H. et. al. *Immunology Today,* 7, 45–56 (1986)). IL-1β is synthesized as a cell associated precursor polypeptide (pro-IL-1β) that is unable to bind IL-1 receptors and is biologically inactive (Mosley et al., *J. Biol. Chem.* 262:2941–2944 (1987)). By inhibiting conversion of precursor IL-1β to mature IL-1β, the activity of interleukin-1 can be inhibited. Interleukin-1β converting enzyme (ICE) is a protease responsible for the activation of interleukin-1β (IL-1β) (Thornberry, N. A., et al., *Nature* 356: 768 (1992); Yuan, J., et al., *Cell* 75: 641 (1993)). ICE is a substrate-specific cysteine protease that cleaves the inactive prointerleukin-1 to produce the mature IL-1. The genes that encode for ICE and CPP32 are members of the mammalian ICE/Ced-3 family of genes which presently includes at least twelve members: ICE, CPP32/Yama/Apopain, mICE2, ICE4, ICH1, TX/ICH-2, MCH2, MCH3, MCH4, FLICE/MACH/MCH5, ICE-LAP6 and $ICE_{rel}III$. The proteolytic activity of this family of cysteine proteases, whose active site cysteine residue is essential for ICE-mediated apoptosis, appears critical in mediating cell death (Miura et al., *Cell* 75: 653–660 (1993)). This gene family has recently been named caspases (Alnernri, E. S. et al. *Cell,* 87:171 (1996)).

IL-1 is also a cytokine involved in mediating a wide range of biological responses including inflammation, septic shock, wound healing, hematopoiesis and growth of certain leukemias (Dinarello, Calif., *Blood* 77:1627–1652 (1991); diGiovine et al., *Immunology Today* 11:13 (1990)).

Many potent caspase inhibitors have been prepared based on the peptide substrate structures of caspases. However, in contrast to their potency in vitro, no inhibitors with good efficacy ($IC_{50}<1$ μM) in whole-cell models of apoptosis have been reported (Thornberry, N. A. *Chem. Biol.* 5:R97–103 (1998)). Therefore the need exists for cell death inhibitors that show efficacy ($IC_{50}<1$ μM) in whole-cell models of apoptosis and are active in animal models of apoptosis. These inhibitors thus can be employed as therapeutic agents to treat disease states in which regulated cell death and the cytokine activity of IL-1 play a role.

WO 93/05071 disclosed peptide ICE inhibitors with the formula:

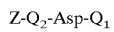

wherein Z is an N-terminal protecting group; $Q_2$ is 0 to 4 amino acids such that the sequence $Q_2$-Asp corresponds to at least a portion of the sequence Ala-Tyr-Val-His-Asp; $Q_1$ comprises an electronegative leaving group. Exemplary dipeptides are Boc-His-Asp-$CH_2F$, Boc-Tyr-Asp-$CH_2F$, Boc-Phe-Asp-$CH_2F$, Ac-His-Asp-$CH_2F$, Ac-Tyr-Asp-$CH_2F$, Ac-Phe-Asp-$CH_2F$, Cbz-His-Asp-$CH_2F$, Cbz-Tyr-Asp-$CH_2F$ and Cbz-Phe-Asp-$CH_2F$.

WO 96/03982 disclosed aspartic acid analogs as ICE inhibitors with the formula:

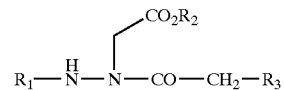

wherein $R_2$ is H or alkyl; $R_3$ is a leaving group such as halogen; $R_1$ is heteroaryl-CO or an amino acid residue.

U.S. Pat. No. 5,585,357 disclosed peptidic ketones as ICE inhibitors with the formula:

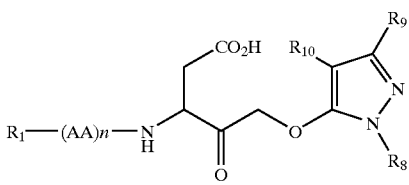

wherein n is 0–2; each AA is independently L-valine or L-alanine; $R_1$ is selected from the group consisting of N-benzyloxycarbonyl and other groups; $R_8$, $R_9$, $R_{10}$ are each independently hydrogen, low alkyl and other groups.

Revesz et al. (*Tetrahedron Lett.* 35, 9693–9696, 1994) reported the preparation of ethyl ester tripeptide:

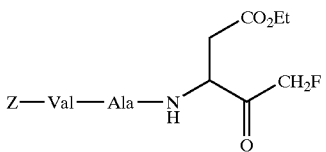

as a prodrug of the corresponding acid which is a potent ICE inhibitor.

SUMMARY OF THE INVENTION

The invention relates to dipeptides of formula I:

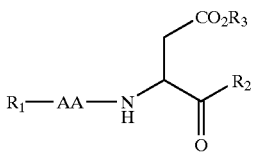

wherein $R_1$ is an N-terminal protecting group; AA is a residue of any natural or non-natural α-amino acid, β-amino acid, derivatives of an α-amino acid or β-amino acid; $R_2$ is H or $CH_2R_4$ where $R_4$ is an electronegative leaving group, and $R_3$ is alkyl or H, provided that AA is not His, Tyr, Pro or Phe.

The invention relates to the discovery that the dipeptide-based caspase inhibitors represented by Formula I, though less potent in enzyme assays than tri- and tetrapeptide inhibitors on the enzymes, are surprisingly potent inhibitors of apoptosis in cell based systems. These compounds are systemically active in vivo and are potent inhibitors of antiFas-induced lethality in a mouse liver apoptosis model and have robust neuroprotective effects in a rat model of ischemic stroke.

The invention also relates to the use of the dipeptides of the invention for reducing, preventing or treating maladies in which apoptotic cell death is either a causative factor or a result. Examples of uses for the present invention include protecting the nervous system following focal ischemia and global ischemia; treating neurodegenerative disorders such as Alzheimer's disease, Huntington's Disease, prion diseases, Parkinson's Disease, multiple sclerosis, amyotrophic lateral sclerosis, ataxia, telangiectasia, and spinobulbar atrophy; treating heart disease including myocardial infarction, congestive heart failure and cardiomyopathy; treating retinal disorders; treating autoimmune disorders including lupus erythematosus, rheumatoid arthritis, type I diabetes, Sjögren's syndrome and glomerulonephritis; treating polycystic kidney disease and anemia/erythropoiesis; treating immune system disorders, including AIDS and SCIDS; reducing or preventing cell, tissue and organ damage during transplantation; reducing or preventing cell line death in industrial biotechnology; reducing or preventing alopecia (hair loss); and reducing the premature death of skin cells.

The present invention provides pharmaceutical compositions comprising a compound of Formula I in an effective amount to reduce apoptotic cell death in an animal.

The present invention also provides preservation or storage solutions for mammalian organs or tissue, or growth media for mammalian or yeast cells, wherein an effective amount of a compound of Formula I is included in said solutions or media in order to reduce apoptotic cell death in said organs, tissue or cells.

BRIEF DESCRIPTION OF THE FIGURES

FIGS. 7A–7E depict the results of PARP cleavage assays in Jurkat cells. Compound 1=Cbz-Val-Asp(OMe)-$CH_2F$. Compound 2=Cbz-Asp(OMe)-Glu(OMe)-Val-Asp(OMe)-$CH_2F$ (SEQ ID NO:1). Compound 3=Cbz-Glu(OMe)-Val-Asp(OMe)-$CH_2F$. Compound 4=Cbz-Ile-Glu(OMe)-Thr-Asp(OMe)-$CH_2F$ (SEQ ID NO:2). Compound 5=BOC-Asp(OMe)-$CH_2F$. Compound 6=Cbz-Asp-α-([2,6-dichlorobenzoyloxy]methylketone). Compound 7=Cbz-Val-Ala-Asp(OMe)-$CH_2F$.

DETAILED DESCRIPTION OF THE INVENTION

Figure 1A:
FIGS. 1A–1G depict photographs of HeLa cells challenged with cycloheximide (CHX) and DMSO (FIG. 1A), tumor necrosis factor-alpha (TNF-α)/CHX and DMSO (FIG. 1B); 50 μM BOC-Asp(OMe)-$CH_2F$, TNF-α/CHX (FIG. 1C); 50 μM Cbz-Val-Asp(OMe)-$CH_2F$, TNF-α/CHX (FIG. 1D); 50 μM Cbz-Glu(OMe)-Val-Asp(OMe)-$CH_2F$, TNF-α/CHX (FIG. 1E); 50 μM Cbz-Asp(OMe)-Glu(OMe)-Val-Asp(OMe)-$CH_2F$ (SEQ ID NO:1), TNF-α/CHX (FIG. 1F); and DMSO (FIG. 1G).
Figure 1B:
Figure 1C:
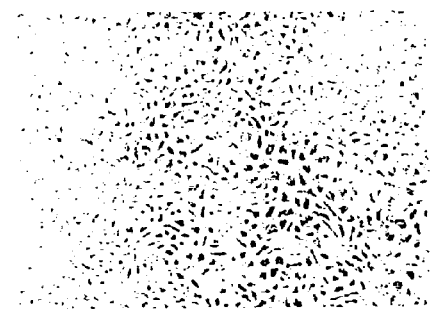
Figure 1D:
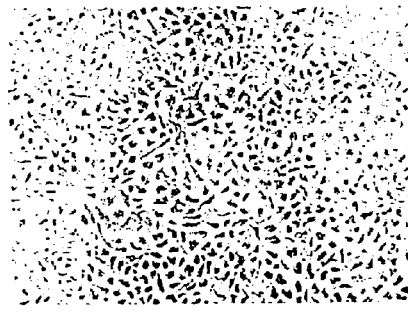
Figure 1E:
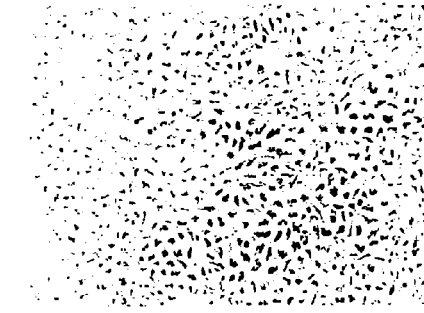
Figure 1F:
Figure 1G:
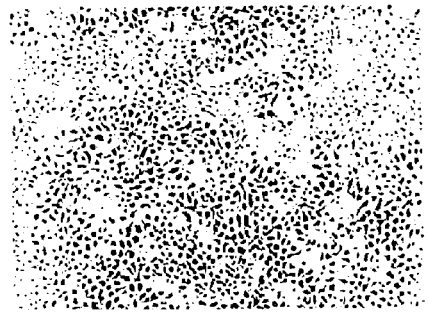
Figure 2A:
FIGS. 2A–2G depict photographs of HeLa cells challenged with cycloheximide (CHX) and DMSO (FIG. 2A), TNF-α/CHX and DMSO (FIG. 2B); 5 μM BOC-Asp(OMe)-$CH_2F$, TNF-α/CHX (FIG. 2C); 5 μM Cbz-Val-Asp(OMe)-$CH_2F$, TNF-α/CHX (FIG. 2D); 5 μM Cbz-Glu(OMe)-Val-Asp(OMe)-$CH_2F$, TNF-α/CHX (FIG. 2E); 5 μM Cbz-Asp(OMe)-Glu(OMe)-Val-Asp(OMe)-$CH_2F$ (SEQ ID NO:1), TNF-α/CHX (FIG. 2F); and DMSO (FIG. 2G).
Figure 2B:
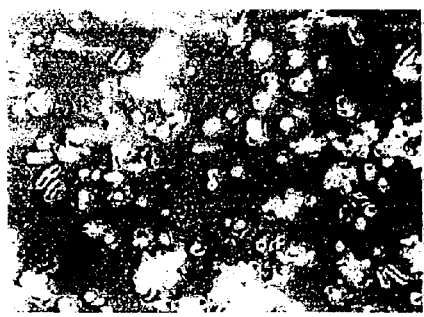
Figure 2C:
Figure 2D:
Figure 2E:
Figure 2F:
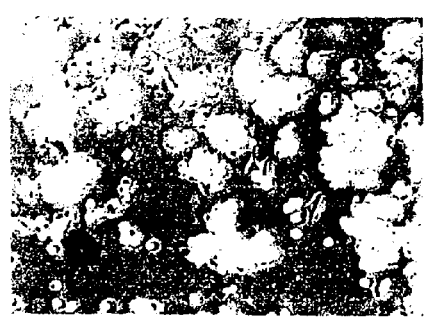
Figure 2G:
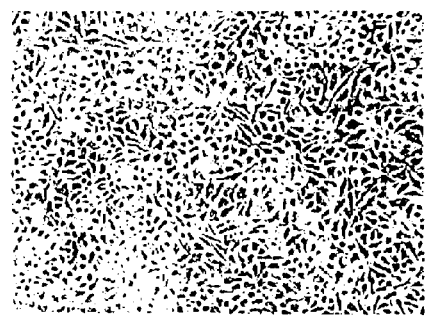
Figure 3A:
FIGS. 3A–3G depict photographs of HeLa cells challenged with cycloheximide (CHX) and DMSO (FIG. 3A), TNF-α/CHX and DMSO (FIG. 3B); 0.5 μM BOC-Asp(OMe)-$CH_2F$, TNF-α/CHX (FIG. 3C); 0.5 μM Cbz-Val-Asp(OMe)-$CH_2F$, TNF-α/CHX (FIG. 3D); 0.5 μM Cbz-Glu(OMe)-Val-Asp(OMe)-$CH_2F$, TNF-α/CHX (FIG. 3E); 0.5 μM Cbz-Asp(OMe)-Glu(OMe)-Val-Asp(OMe)-$CH_2F$ (SEQ ID NO:1), TNF-α/CHX (FIG. 3F); and DMSO (FIG. 3G).
Figure 3B:
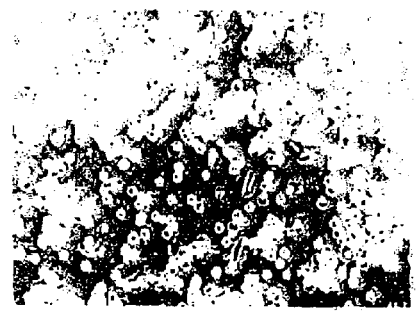
Figure 3C:
Figure 3D:
Figure 3E:
Figure 3F:
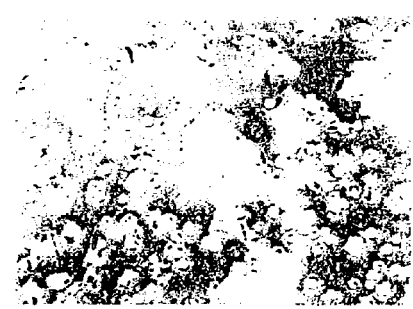
Figure 3G:
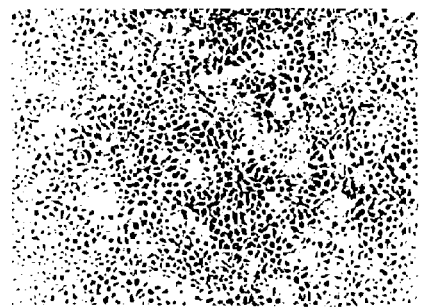

The inhibitors of apoptotic cell death of the present invention are compounds having the general Formula I:

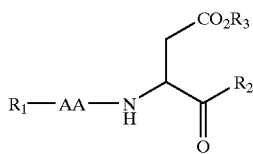

I or pharmaceutically acceptable salts or prodrugs thereof, wherein:

$R_1$ is an N-terminal protecting group including t-butyloxycarbonyl, acetyl, and benzyloxycarbonyl; AA is a residue of any natural or non-natural α-amino acid, or β-amino acid, or a derivative of an α-amino acid or β-amino acid, e.g. Gly, Thr, Glu, Lys, Arg, Ser, Asn, Gln, Val, Ala, Leu, Ile, Met, and β-amino acids such as β-Ala, and which is not His, Tyr, Pro or Phe; $R_2$ is H or $CH_2R_4$, $R_4$ is an electronegative leaving group such as F, Cl, TsO—, MeO—, ArO—, ArCOO, ArN—, and ArS—; and $R_3$ is alkyl or H.

With respect to $R_3$, preferred alkyl groups are $C_{1-6}$ alkyl groups, e.g. methyl, ethyl, propyl, isopropyl, isobutyl, pentyl and hexyl groups.

The invention relates to the discovery that the dipeptide-based caspase inhibitors represented by Formula I, though less potent than tri- and tetrapeptide inhibitors on the enzymes, are surprisingly potent inhibitors of apoptosis in cell based systems. These compounds are systemically active in vivo and are potent inhibitors of antiFas-induced lethality in a mouse liver apoptosis model and have robust neuroprotective effects in a rat model of ischemic stroke. These inhibitors will slow or block cell death in a variety of clinical conditions and industrial applications in which the loss of cells, tissues or entire organs occurs. Therefore, the invention is also related to methods of treating, preventing or reducing conditions in which apoptosis plays a role. These conditions are more fully described below.

The methods comprise administering to an animal in need of such treatment an inhibitor of the present invention, or a pharmaceutically acceptable salt or prodrug thereof, in an amount effective to inhibit apoptotic cell death.

Preferred embodiments of the compounds that may be employed as inhibitors of apoptosis are represented by Formula II:

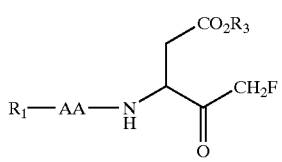

II or pharmaceutically acceptable salts or prodrugs thereof wherein AA, $R_1$ and $R_3$ are as defined previously with respect to Formula I.

Preferred $R_1$ is t-butyloxycarbonyl, acetyl and benzyloxycarbonyl. Preferred $R_3$ is H, Me, Et or t-Bu. Preferred AA is Val, Ala, Leu, Ile, Met, and β-amino acids such as β-Ala.

Exemplary preferred inhibitors of apoptosis having Formula I include. without limitation:

Boc-Ala-Asp-CH$_2$F,
Boc-Val-Asp-CH$_2$F,
Boc-Leu-Asp-CH$_2$F,
Ac-Val-Asp-CH$_2$F,
Ac-Ile-Asp-CH$_2$F,
Ac-Met-Asp-CH$_2$F,
Cbz-Val-Asp-CH$_2$F,
Cbz--Ala-Asp-CH$_2$F,
Cbz-Leu-Asp-CH$_2$F,
Cbz-Ile-Asp-CH$_2$F,
Boc-Ala-Asp(OMe)-CH$_2$F,
Boc-Val-Asp(OMe)-CH$_2$F,
Boc-Leu-Asp(OMe)-CH$_2$F,
Ac-Val-Asp(OMe)-CH$_2$F,
Ac-Ile-Asp(OMe)-CH$_2$F,
Ac-Met-Asp(OMe)-CH$_2$F,
Cbz-Val-Asp(OMe)-CH$_2$F,
Cbz--Ala-Asp(OMe)-CH$_2$F,
Cbz-Leu-Asp(OMe)-CH$_2$F, and
Cbz-Ile-Asp(OMe)-CH$_2$F.

Certain of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts such as hydrochloride, hydrobromide, phosphate, sulphate, citrate, lactate, tartrate, maleate, fumarate, mandelate and oxalate.

Examples of prodrugs include compounds of Formula I–II wherein $R_3$ is an alkyl group or substituted alkyl group such as CH$_2$OCH$_3$. Further, in the cases where AA contains a carboxylic acid group, examples of prodrugs of formula I–II wherein $R_3$ is H includes compounds in which either or both carboxyl groups are esterified (e.g. with a $C_{1-6}$ alcohol) or are in the form of the corresponding amides (e.g. with a $C_{1-6}$ amine).

The invention is also directed to a method for treating disorders responsive to the inhibition of apoptosis in animals suffering thereof. Particular preferred embodiments of compounds for use in the method of this invention are represented by previously defined Formula II.

The compounds of this invention may be prepared using methods known to those skilled in the art. Specifically, compounds with Formulae I–II can be prepared as illustrated by exemplary reactions in Scheme 1. The intermediate 1 was prepared according to Revesz et al. (*Tetrahedron Lett.* 35, 9693–9696, 1994). Coupling of 1 with a N-protected amino acid such as Z-Val-OH gave amide 2 which was oxidized by Dess-Martin reagent according to Revesz et al. (*Tetrahedron Lett.* 35, 9693–9696, 1994) to give 3 as a mixture of diasteriomers. Acid catalyzed cleavage of the ester gave the free acid 4 which was converted to ester 5.

Scheme 1

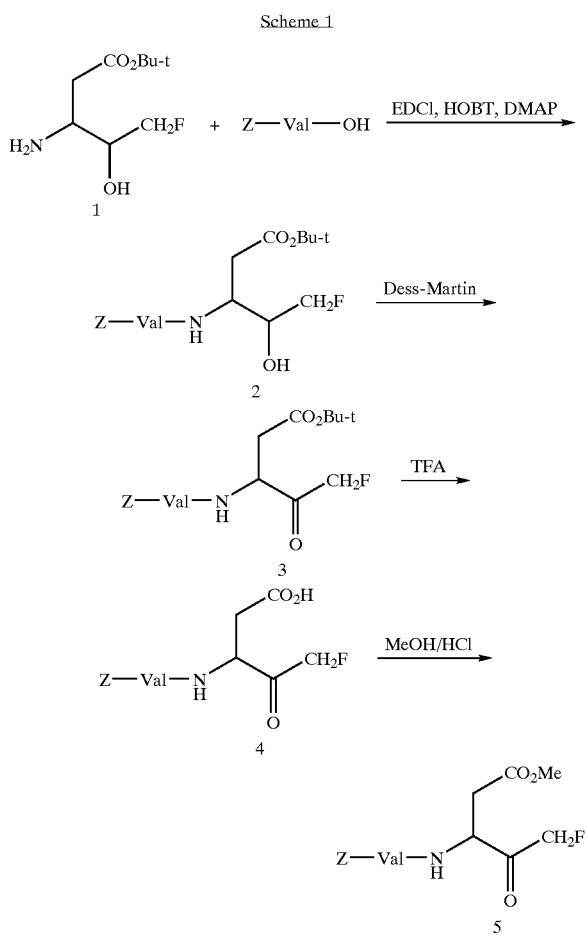

An important aspect of the present invention is the discovery that compounds having Formulae I–II are potent inhibitors of apoptosis. Therefore, these inhibitors are expected to slow or block cell death in a variety of clinical conditions in which the loss of cells, tissues or entire organs occurs.

The cell death inhibitors of the present invention can be used to reduce or prevent cell death in the nervous system (brain, spinal cord, and peripheral nervous system) under various conditions of ischemia and excitotoxicity, including, but not limited to, focal ischemia due to stroke and global ischemia due to cardiac arrest, as well as spinal cord injury (Emery et al. *J. Neurosurgery*, 89: 911–920 (1998)). One particular usage is to treat the effects of oxygen deprivation which can occur during the birth of infants in high-risk labors. The cell death inhibitors can also be used to reduce or prevent cell death in the nervous system due to traumatic injury (such as head trauma), viral infection or radiation-induced nerve cell death (for example, as a side-effect of cancer radiotherapy). The cell death inhibitors can also be used to reduce or prevent cell death in a range of neurodegenerative disorders, including but not limited to Alzheimer's disease (Mattson et al. *Brain Res.* 807: 167–176 (1998)), Huntington's Disease, Parkinson's Disease, multiple sclerosis, amyotrophic lateral sclerosis, and spinobulbar atrophy. The in vivo neuroprotective properties of cell death inhibitors of the invention can be tested in a rat transient focal brain ischemia model (Xue et al., *Stroke* 21: 166 (1990)).

The cell death inhibitors of the invention can be used to reduce or prevent cell death in any condition which potentially results in the death of cardiac muscle (Black et al., *J. Mol. Cel. Card.* 30: 733–742 (1998) and Maulik et al. *Free Radic. Biol. Med.* 24: 869–875 (1998)). This includes myocardial infarction due to myocardial ischemia and reperfusion, congestive heart failure and cardiomyopathy. One particular application is to reduce or prevent myocardial cell death as occurs in certain viral infections of the heart.

The in vivo activity of the cell death inhibitors of the invention can be tested using the "mouse liver apoptosis" model described by Rodriguez et al. (Rodriguez et al., *J. Exp. Med.*, 184:2067–2072 (1996)). In this model, mice are treated intravenously (IV) with an antiFas antibody which induces massive apoptosis in the liver and other organs, leading to generalized organ failure and death. This model is useful for indirectly testing the systemic bioavailability of the cell death inhibitors of the invention, as well as their in vivo anti-apoptotic properties. The cell death inhibitors of the invention therefore can be used to reduce or prevent apoptosis of liver cells (Jones et al. *Hepatology* 27: 1632–42 (1998)) such as in sepsis (Jaeschke et al. *J. Immunol.* 160: 3480–3486 (1998)) and hereditary tyrosinemia type 1 (HT1) (Kubo et al. *Proc. Natl. Acad Sci. USA*, 95: 9552–9557 (1998). The cell death inhibitors of the invention also can be used to treat hepatitis (Suzuki, *Proc. Soc. Exp. Biol. Med.* 217: 450–454 (1998)).

The cell death inhibitors of the invention can be used to reduce or prevent cell death of retinal neurons (Kermer et al. *J. Neurosci.* 18: 4656–4662 (1998) and Miller et al. *Am. J Vet. Res.* 59: 149–152 (1998)) as can occur in disorders which increase intraocular pressure (such as glaucoma) or retinal disorders associated with the aging process (such as age-related macular degeneration). The inhibitors can also be used to treat hereditary degenerative disorders of the retina, such as retinitis pigmentosa.

The cell death inhibitors of the invention can also be used to reduce or prevent cell death in the kidney. This includes renal amyloidosis (Hiraoka et al. *Nippon Jinzo Gakkai Shi*, 40: 276–83 (1998)), acute renal failure (Lieberthal et al. *Semin Nephrol.* 18: 505–518 (1998)), murine tubular epithelial cell death induced by cyclosporine, A (Ortiz et al. *Kidney International Supp.* 68: S25-S29 (1998)) and HIV-induced nephropathy (Conaldi et al. *J. Clin. Invest.* 102: 2041–2049 (1998)).

The cell death inhibitors of the invention can also be used to reduce or prevent cell death of buccal mucosa due to chronic alcohol ingestion (Slomiany et al. *Biochem. Mol. Biol. Int.* 45: 1199–1209 (1998)).

The cell death inhibitors of the invention can also be used to reduce or prevent cell death in plants (Richberg et al. *Curr. Opin. Plant Biol.* 1: 480–485 (1998)), such as plant cell death due to pathogens (Pozo et al. *Curr. Biol.* 8: 1129–1132 (1998) and Greenberg et al. *Cell*, 77: 551–563 (1994)).

The cell death inhibitors of the invention can also be used to reduce or prevent cell death due to radiation and ultraviolet-irradiation (Sheikh et al. *Oncogene*, 17: 2555–2563 (1998)).

The cell death inhibitors of the invention can also be used to reduce or prevent apoptotic death of bone marrow cells in myelodysplastic syndromes (MDS) (Mundle et al., *Am. J Hematol.* 60: 36–47 (1999)).

The cell death inhibitors of the invention can also be used to reduce or prevent premature death of cells of the immune system, and are particularly useful in treating immune deficiency disorders, such as acquired immune deficiency syndrome (AIDS), severe combined immune deficiency syndrome (SCIDS) and related diseases. The cell death inhibitors can also be used to treat radiation-induced immune suppression.

Transplantation of human organs and tissues is a common treatment for organ failure. However, during the transplantation process, the donor organ or tissue is at risk for cell death since it is deprived of its normal blood supply prior to being implanted in the host. This ischemic state can be treated with cell death inhibitors by infusion into the donor organ or tissue, or by direct addition of the cell death inhibitors to the organ/tissue storage medium. Cell death inhibitors may also be used to reduce or prevent cell death in the donor organ/tissue after it has been transplanted to protect it from the effects of host immune cells which kill their targets by triggering apoptosis. The cytoprotective effects of cell death inhibitors can also be used to prevent the death of human or animal sperm and eggs used in in vitro fertilization procedures. These inhibitors can be used during the harvesting process and can also be included in the storage medium.

Mammalian cell lines and yeast cells are commonly used to produce large amounts of recombinant proteins (such as antibodies, enzymes or hormones) for industrial or medicinal use. The lifespan of some of these cell lines is limited due to growth conditions, the nature of the recombinant molecule being expressed (some are toxic) and other unknown factors. The lifespans of industrial cell lines can be extended by including these cell death inhibitors in the growth medium in a concentration range of 10–200 mM.

The factors governing hair growth and loss are largely unknown. There is some evidence, however, that hair follicle regression (referred to as catagen) may be due at least partially to apoptosis. Therefore, it is contemplated that the cell death inhibitors of the present invention can be used to treat hair loss that occurs due to various conditions, including but not limited to male-pattern baldness, radiation-induced or chemotherapy-induced hair loss, and hair loss due to emotional stress. There is also evidence that apoptosis may play a role in the loss of hair color. Therefore, it is contemplated that the cell death inhibitors of the present invention can also be used in treating or preventing cases of premature graying of the hair.

The death of skin epithelial cells can occur after exposure to high levels of radiation, heat or chemicals. It is contemplated that the cell death inhibitors of the present invention can be used to treat, reduce or prevent this type of skin damage. In one particular application, the cell death inhibitors can be applied in an ointment to treat acute overexposure to the sun and to prevent blistering and peeling of the skin.

Goldberg et al. (*Nature Genetics* 13: 442–449 (1996)) reported recently that huntingtin, a protein product of Huntington's disease (HD) gene, can be cleaved by CPP32 but not ICE. The mutation underlying HD is an expansion of a CAG trinucleotide at the 5' end of the HD gene. The trinucleotide expansion exceeding 36 repeats is associated with the clinical presentation of HD. The CAG expansion promotes cleavage of huntingtin by CPP32, thus links the role of CPP32 in the apoptotic cell death in HD. Compounds of the present invention with CPP32 inhibiting activity will be useful in blocking CPP32 induced apoptotic cell death, thus in preventing and treating HD and other disorders characterized by expansion of trinucleotide repeats such as myotonic dystrophy, fragile X mental retardation, spinobulbar muscular atrophy, spinocerebellar atoxia type I and Dentato-Rubro pallidoluysian atrophy.

Compositions within the scope of this invention include all compositions wherein the compounds of the present invention are contained in an amount which is effective to achieve its intended purpose. While individual needs vary, determination of optimal ranges of effective amounts of each component is with the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for apoptosis-mediated disorders, e.g., neuronal cell death, heart disease, retinal disorders, polycystic kidney disease, and immune system disorders. Preferably, about 0.01 to about 10 mg/kg is orally administered to treat or prevent such disorders. For intramuscular injection, the dose is generally about one-half of the oral dose. For example, for treatment or prevention of neuronal cell death, a suitable intramuscular dose would be about 0.0025 to about 15 mg/kg, and most preferably, from about 0.01 to about 10 mg/kg.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular cell death inhibitors of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular cell death inhibitors of the present invention with a solution of a pharmaceutically acceptable non-toxic base such as sodium hydroxide, potassium hydroxide, choline hydroxide, sodium carbonate and the like.

The pharmaceutical compositions of the invention may be administered to any animal which may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal or intracranial routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules. the active compounds are preferably dissolved or suspended in suitable liquids, such as fatty oils, or liquid paraffin. In addition, stabilizers may be added Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. Buffers such as Tris may be present. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin damage, such as that caused by exposure to high levels of radiation, including ultraviolet radiation, heat or chemicals.

One or more additional substances which have therapeutic effects on the skin may also be incorporated in the compositions. Thus, the composition may also contain one or more compounds capable of increasing cyclic-AMP levels in the skin. Suitable compounds include adenosine or a nucleic acid hydrolysate in an amount of about 0.1–1% and papaverine, in an amount of about 0.5–5%, both by weight based on the weight of the composition. Also suitable are β-adrenergic agonists such as isoproterenol, in an amount of about 0.1–2% or cyclic-AMP, in an amount of about 0.1–1%, again both by weight based on the weight of the composition. Other suitable types of additional active ingredients which may be incorporated in the compositions of this invention include any compounds known to have a beneficial effect on skin. Such compounds include retinoids such as Vitamin A, in an amount of about 0.003–0.3% by weight and chromanols such as Vitamin E or a derivative thereof in an amount of about 0.1–10% by weight, both based on the weight of the composition. Additionally, anti-inflammatory agents and keratoplastic agents may be incorporated in the cosmetic composition. A typical anti-inflammatory agent is a corticosteroid such as hydrocortisone or its acetate in an amount of about 0.25–5% by weight, or a corticosteroid such as dexamethasone in an amount of about 0.025–0.5% by weight, both based on the weight of the composition. A typical keratoplastic agent is coal tar in an amount of about 0.1–20% or anthralin in an amount of about 0.05–2% by weight, both based on the weight of the composition.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or polyethylene glycol.

In addition, these compositions may include other medicinal agents, growth factors, wound sealants, carriers, etc., that are known or apparent to those skilled in the art. The compositions of the invention are administered to a warm-blooded animal, such as human, already suffering from a skin damage, such as a burn, in an amount sufficient to allow the healing process to proceed more quickly than if the host were not treated. Amounts effective for this use will depend on the severity of the skin damage and the general state of health of the patient being treated. Maintenance dosages over a prolonged period of time may be adjusted as necessary. For veterinary uses, higher levels may be administered as necessary.

In the case of an animal suffering from decreased hair growth, the compositions of the invention are administered in an amount sufficient to increase the rate of hair growth. Amounts effective for this use will depend on the extent of decreased hair growth, and the general state of health of the patient being treated. Maintenance dosages over a prolonged period of time may be adjusted as necessary. For veterinary uses, higher levels may be administered as necessary.

When the compounds are to be administered to plants, they may be applied to the leaves and/or stems and/or flowers of the plant, e.g. by spraying. The compounds may be spayed in particulate form or dissolved or suspended in an appropriate carrier, e.g. in water or an oil-water emulsion. The compounds may also be combined with the soil of the plant. In this embodiment, the compounds are taken up by the roots of the plant.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1 t-Butyl 5-fluoro-4-hydroxy-3-nitropentanoate

A solution of oxalic acid (1.9 mL, 21.8 mmol) in dry $CH_2Cl_2$ (100 mL) was cooled to −78° C., a solution of DMSO (3.0 mL, 42.3 mmol) in dry $CH_2Cl_2$ (10 mL) was added with stirring in such a rate that the temperature was kept at −50 to −60° C. After 5 min stirring, a solution of 2-fluoroethanol (1.2 mL, 18.4 mmol) in dry $CH_2Cl_2$ (10 mL) was added, and stirring was continued for an additional 15 min, then dry $Et_3N$ (13.5 mL) was added. The reaction mixture was stirred for 15 min, then allowed to warm to rt. To the reaction mixture was added a solution of t-butyl 3-nitropropionate (2.87 g, 16.38 mmol) in $CH_2Cl_2$ (20 mL). The reaction mixture was stirred at rt for 3 h, then poured into water (100 mL). The organic layer was separated and the aqueous was extracted with $CH_2Cl_2$ (2×50 mL). The $CH_2Cl_2$ solution was washed with brine, dried and evaporated. The residue was purified by chromatography twice over silica gel (hexane-EtOAc, 7:3) to give 950 mg (24.5%) of the titled product as a colorless viscous oil. $^1$H NMR ($CDCl_3$), 1.450 (s, 9H), 2.80–2.90 (m, 2H), 3.12–3.20 (m, 1H), 4.41–4.59 (m, 2H), 4.57–4.59 (m, 1H), 4.95–5.01 (m, 1H).

EXAMPLE 2 t-Butyl 3-amino-5-fluoro-4-hydroxy-pentanoate

To a solution of t-butyl 5-fluoro-4-hydroxy-3-nitropentanoate (950 mg, 4.0 mmol) in MeOH (20 mL) was added Raney Ni (about 200 mg), the mixture was shaken under $H_2$ (30–35 psi) at rt for 18 h. It was filtered and the catalyst was washed with MeOH (2×10 mL). The MeOH solution was evaporated and the residue was purified by chromatography over silica gel (EtOAc-MeOH, 10:1) to give 840 mg (96%) of the titled compound as a yellowish viscous oil. $^1$HNMR ($CDCl_3$), 1.450 (s, 9H), 2.12 (bs, 3H, OH and $NH_2$), 2.28–2.38 (m, 1H), 2.47–2.57 (m, 1H), 3.24–3.30 (m, 1H), 3.54–3.76 (m, 1H), 4.38–4.48 (m, 1H), 4.54–4.61 (m, 1H).

EXAMPLE 3 t-Butyl 3-(Cbz-Val-amido)-5-fluoro-4-hydroxy-pentanoate

To a solution of Cbz-Valine (396 mg, 1.58 mmol) in THF (20 mL) was added 1-(3-dimethylaminopropyl)-3-ethylcarbodiimide (EDCI) (300 mg, 1.57 mmol), 1-hydroxybenzotriazole hydrate (HOBT) (240 mg, 1.57 mmol) and dimethylaminopyridine (DMAP) 129 mg 1.06 mmol). The resulting mixture was stirred for 5 min, then was added a solution of t-butyl 3-amino-5-fluoro-4-hydroxy-pentanoate (215 mg, 1.04 mmol) in THF (10 mL) and it was stirred at rt for 18 h. The mixture was filtered and the THF solution was evaporated, and the residue was purified by chromatography over silica gel (hexane-EtOAc, 3:2) to give 290 mg (68%) of the titled compound as a white solid. $^1$HNMR ($CDCl_3$), 0.905 (d, 3H, J=7), 0.965 (d, 3H, J=7), 1.428 (s, 9H), 2.07–2.16 (m, 1H), 2.50–2.57 (m, 1H), 2.64–2.70 (m, 1H), 3.52 (bs, 1H, OH), 3.92–3.96 (m, 2H), 4.20–4.27 (m, 1H), 4.40 (bs, 1H),4.49 (bs, 1H), 5.10 (s, 2H), 5.31–5.4 (m, 1H, NH), 6.86–6.93 (m, 1H, NH), 7.350(s, 5H).

EXAMPLE 4

Z-Val-Asp-fmk t-butyl ester

To a suspension of Dess-Martin periodinane (485 mg, 1.14 mmol) in $CH_2Cl_2$ (20 mL) was added a solution of t-butyl 3-(Cbz-Val-amido)-5-fluoro-4-hydroxy-pentanoate (230 mg, 0.52 mmol) in $CH_2Cl_2$ (12 mL), and the resulting white mixture was stirred at rt for 40 min, then poured into 25 mL of saturated aq $NaHCO_3$ solution containing 1.26 g (8 mmol) of $Na_2S_2O_3$. The resulting mixture was stirred for 20 min, the resulting clear $CH_2Cl_2$ solution was separated and the aqueous was extracted with $CH_2Cl_2$ (2×25 mL). The $CH_2Cl_2$ solution was washed with brine and evaporated, then the residue was purified by chromatography over silica gel (hexane-EtOAc, 3:2) to give 190 mg (83%) of titled compound as a white solid. $^1$HNMR ($CDCl_3$), 0.91–0.97 (m, 6H), 1.415 (s, 9H), 2.10–2.20 (m, 1H), 2.70–2.77 (m, 1H), 2.95–3.01 (m, 1H), 3.98–4.06 (m, 1H), 4.87–5.28 (m, 6H), 6.95–7.01 (m, 1H), 7.350 (s, 5H).

EXAMPLE 5

Z-Val-Asp-fmk

To a solution of the Z-Val-Asp-fmk t-butyl ester (180 mg, 0.41 mmol) in dry $CH_2Cl_2$ (5 mL) was added $F_3CCO_2H$ (1.0 mL), and it was stirred at rt for 40 min, then evaporated. The residue was purified by chromatography over silica gel (EtOAc-MeOH, 10:1) to give 120 mg (76%) of the titled compound as a white solid. $^1$HNMR (DMSO-$d_6$), 0.81–0.84 (m, 6H), 1.87–1.96 (m, 1H), 2.47–2.67 (m, 2H), 3.77–3.87 (m, 1H), 4.47–4.59 (m, 1H), 4.91–5.16 (m, 4H), 7.25–7.42 (s, 5H), 8.40–8.49 (m, 1H).

The following compounds were obtained by using the same procedure as described in Example 3–5:

EXAMPLE 6

Z-Leu-Asp-fmk

White solid. $^1$H NMR ($CDCl_3$), 0.87 (m, 6H), 1.11 (m, 1H), 1.47 (m, 1H), 1.81 (m, 1H), 2.7 (m, 1H), 2.95 (m, 1H), 4.10 (m, 1H), 4.80–5.20 (m, 6H), 7.31 (s, 5H).

EXAMPLE 7

Z-Ile-Asp-fmk

White solid. $^1$H NMR (CDCl$_3$), 0.85–0.96 (m, 6H), 1.14–1.26 (m, 1H), 1.422 (s, 9H), 1.87–2.04 (m, 1H), 2.70–2.77 (m, 2H), 2.93–3.00 (m, 1H), 4.02–4.13 (m, 1H), 4.80–5.30 (s, 6H), 6.96 (m, 1H), 7.35 (s, 5H).

EXAMPLE 8

Z-Ala-Asp-fmk

White solid. $^1$H NMR (DMSO-d$_6$), 1.160 (d, 3H, J=7), 2.54–2.70 (m, 2H), 4.00 (m, 1H), 4.54 (m, 1H), 5.10–5.30 (m, 3H), 7.235 (s, 5H), 8.46–8.52 (m, 1H).

EXAMPLE 9

Ac-Val-Asp-fmk

White solid. $^1$H NMR (DMSO-d$_6$), 0.80–0.84 (m, 6H), 1.85–1.97 (m, 4H), 2.56–2.75 (m, 2H), 4.00–4.45 (m, 4H), 5.00–5.30 (m, 2H), 7.85–8.00 (m, 1H), 8.53–8.60 (m, 1H).

EXAMPLE 10

Z-N-Me-Val-Asp-fmk

White solid. $^1$H NMR (DMSO-d$_6$), 0.765 (d, 3H, J=7), 0.832 (d, 3H, J=7), 2.06 (m, 1H), 2.57–2.85 (m, 5H), 4.21 (m, 1H), 4.63 (m, 1H), 5.02–5.18 (m, 4H), 7.337 (s, 5H), 8.850 (m, 1H).

EXAMPLE 11

Z-Ala-Asp-fmk

White solid. $^1$H NMR (DMSO-d$_6$), 2.30 (t, 2H, J=7), 2.48–2.70 (m, 3H), 3.17 (m, 2H), 4.41–4.60 (m, 2H), 4.98–5.30 (m, 3H), 5.40 (m, 1H), 6.63 (m, 1H), 7.32 (s, 5H), 8.52 (m, 1H).

EXAMPLE 12

Z-Gly-Asp-fmk

White solid. $^1$H NMR (DMSO-d$_6$), 12.50 (s, 1 H), 8.49 (m, 1 H), 7.52 (m, 1 H), 7.33 (s, 5 H), 5.08–5.25 (m, 1 H), 5.01 (s, 2 H), 4.10 (m, 1 H), 3.63 (d, J=6.0 Hz, 2 H), 2.50–2.80 (m, 2 H).

EXAMPLE 13

Z-Phe-Asp-fmk

White solid. $^1$H NMR (DMSO-d$_6$), 8.60 (m, 1 H), 7.60 (m, 1 H), 7.24–7.30 (m, 10 H), 4.92 (m, 3 H), 4.60 (m, 1 H), 4.28 (m, 1 H), 2.90 (m, 2 H), 2.70 (m, 2 H).

EXAMPLE 14

Z-Glu-Asp-fmk

White solid. $^1$H NMR (DMSO-d$_6$), 12.20 (m, 1 H), 8.48 (m, 1 H), 7.56 (m, 1 H), 7.34 (m, 5 H), 5.12 (m, 1 H), 5.01 (s, 2 H), 4.51 (m, 1 H), 3.95 (m, 1 H), 2.71 (m, 2 H), 2.24 (m, 2 H), 1.72–1.82 (m, 2 H).

EXAMPLE 15

Z-Pro-Asp-fmk

White solid. $^1$H NMR (CD$_3$OD): 7.36–7.33 (m, 5 H), 5.13–5.11 (m, 2 H), 4.30 (s, 1 H), 3.58–3.50 (m, 2 H), 2.77–2.64 (m, 2 H), 2.24 (m, 1 H), 1.94 (s, 2 H).

EXAMPLE 16

Z-His-Asp-fmk

White soild. $^1$H NMR (CD$_3$OD): 8.78 (s, 1 H), 7.93 (s, 1 H), 7.36–7.33 (m, 7 H), 5.52 (s, 2 H), 5.10 (s, 2 H), 4.49 (s, 1 H), 3.13–3.05 (m, 2 H), 2.84 (s, 2 H).

EXAMPLE 17

Z-Tyr-Asp-fmk

Z-Tyr(Bu-t)-Asp-fmk t-butyl ester was prepared from Z-Tyr(Bu-t)—OH and t-butyl 3-amino-5-fluoro-4-hydroxypentanoate as described in Examples 3 and 4. To a solution of Z-Tyr(Bu-t)-Asp-fmk t-butyl ester (15 mg, 0.027 mmol) in methylene chloride (1 mL) was added TFA (1 mL). The mixture was stirred at room temperature for 8 h, then at 4 C for 2 days. It was diluted with ethyl acetate (30 mL), washed with water (4×20 mL) and brine, dried over Na$_2$SO$_4$ and concentrated in vacuo to yield the title compound as a yellow solid (10 mg, 0.022 mmol, 83%). $^1$H NMR (DMSO-d$_6$): δ 9.20 (s, 1H), 8.50 (br s, 1H), 7.50 (m, 1H), 7.32–7.03 (m, 7H), 6.63 (d, J=7.5, 2H), 4.94 (s, 2H), 4.55 (m, 1H), 4.15 (m, 1H), 2.90–2.60 (m, 4H).

EXAMPLE 18

Z-Val-Asp-fmk Methyl Ester

Into a solution of Z-Val-Asp-fmk (110 mg, 0.28 mmol) in MeOH (20 mL) cooled in ice-bath was passed slowly a stream of HCl gas, until the solution turned to strong acidic as determined by pH paper. The solution was stirred at rt for 4 h, then evaporated. The residue was purified by chromatography over silica gel (hexane-EtOAc, 3:2) to give 63 mg (55%) of the titled compound as a white solid. $^1$HNMR (CDCl$_3$), 0.91–0.87 (m, 6H), 2.10–2.20 (m, 1H), 2.81–2.88 (m, 1H), 3.02–3.08 (m, 1H), 3.675 and 3.682 (2S, 3H), 3.97–4.01(m, 1H), 4.90–5.25 (m, 6H), 6.94–7.02 (m, 1H), 7.354 (s, 5H).

The following compounds were obtained by using the same procedure as described in Example 18.

EXAMPLE 19

Z-Leu-Asp-fmk Methyl Ester

Colorless viscous oil. $^1$H NMR (CDCl$_3$), 0.92–0.94 (m, 6H), 1.25–1.80 (m, 4H), 2.78–2.82 (m, 1H), 3.00–3.05 (m, 1H), 3.675 (s, 3H), 4.15–4.20 (m, 1H), 4.85–5.10 (m, 6H), 7.10–7.20 (m, 1H), 7.344 (s, 5H).

EXAMPLE 20

Z-Ile-Asp-fmk Methyl Ester

White solid. $^1$H NMR (CDCl$_3$), 0.85–0.96 (m, 6H), 1.14 (m, 1H), 1.46 (s, 1H), 1.87 (m, 1H), 1.91–2.86 (m, 1H), 2.88–3.02 (m, 1H), 3.257 (s, 3H), 4.68–4.06 (m, 1H), 4.80–5.30 (s, 6H), 6.99 (m, 1H), 7.35 (s, 5H).

EXAMPLE 21

Cell Death Assays with HeLa Cells

The cytoprotective properties of Cbz-Val-Asp(OMe) CH$_2$F were tested using HeLa cells challenged with tumor necrosis factor-alpha (TNF-α) and cycloheximide (CHX). This is a well-characterized cell culture model of apoptosis which is commonly used to analyze anti-apoptotic agents.

Two types of experiments were performed: a qualitative assessment of cell death by visualization of the cells using phase contrast microscopy; and a quantitative assessment of cell death using the fluorescent dye calcein AM.

For photomicroscopy, HeLa cells are seeded in 12-well multidishes at a density of 100,000 cells per well in Minimal Essential Medium containing 2 mM glutamine and 10% fetal bovine serum. 24 hours later the plating medium is removed and fresh medium is added containing the cytoprotective test compound at various concentrations. The cells are pre-incubated with test compound for 2 hours at 37° C. in a $CO_2$ incubator and then TNF-α and CHX are added at final concentrations of 25 ng/mL and 30 μg/mL, respectively. After a 24 hour incubation period, the cells are examined visually for evidence of cell death based on cell shape and degree of adherence. Cells are considered dead if they have become rounded up and phase bright and have detached from the substratum. Cells are considered alive if they have retained their normal morphology and remain attached to the substratum.

For quantitative assays, the degree of cell survival in the presence of test compounds is analyzed quantitatively using the indicator dye calcein AM. This dye is taken up and converted to a fluorescent derivative by living cells; the amount of activated dye in each well can then be assayed in a fluorometric plate reader and the degree of fluorescence is used as a measure of the number of surviving cells. For these assays, HeLa cells are seeded in 48-well plates at a density of 25,000 cells per well in 0.4 mL of Minimal Essential Medium containing 2 mM glutamine and 10% fetal bovine serum. 24 hours later the plating medium is removed and 0.5 mL of fresh medium containing test compound at various concentrations is added. The cells are pre-incubated with test compound for 2 hours at 37° C. in a $CO_2$ incubator and then TNF-α and CHX are added at final concentrations of 25 ng/mL and 30 μg/mL, respectively. After a 24 hour incubation period, the cultures are washed twice with serum-free, phenol red-free Ham's F12 to remove dead cells and 125 μL of Ham's F12 containing 8 μM calcein AM is added. The cultures are incubated at room temperature for 1 hour and the fluorescent signal is determined with a BioTek plate reader using filter settings of 485 nm (excitation) and 530 nm (emission). The data are expressed as "Percent Control," which is calculated by the following equation:

Percent Control=(Calcein AM Signal in the Presence of Test Compound+TNF-α and CHX/(Calcein AM Signal in the Presence of CHX Only)×100%

The use of CHX-treated cultures as controls, rather than untreated cultures, allows one to correct for the cytostatic effects of CHX. However, because CHX by itself is also a mild inducer of apoptosis in HeLa cells, strong anti-apoptotic drugs will give a Percent Control value greater than 100%.

Results from a typical qualitative assay are shown in FIGS. 1A–1G, 2A–2G and 3A–3G. In these experiments the cytoprotective potency of Cbz-Val-Asp(OMe)-$CH_2F$ is compared to the cytoprotective potency of BOC-Asp(OMe)-$CH_2F$, Cbz-Glu(OMe)-Val-Asp(OMe)-$CH_2F$, and Cbz-Asp(OMe)-Glu(OMe)-Val-Asp(OMe)-$CH_2F$ (SEQ ID NO:1) at three different concentrations: 0.5, 5 and 50 μM. All of these compounds are the methyl ester derivatives. FIGS. 1A–1G shows that, at a concentration of 50 μM, Cbz-Val-Asp(OMe)-$CH_2F$ (FIG. 1D) completely protects HeLa cells from the apoptotic effects of TNF-α and CHX. At 50 μM, the related peptides BOC-Asp(OMe)-$CH_2F$ (FIG. 1C) and Cbz-Glu(OMe)-Val-Asp(OMe)-$CH_2F$ (FIG. 1E) are also protective. The CPP32 inhibitor, Cbz-Asp(OMe)-Glu(OMe)-Val-Asp(OMe)-$CH_2F$ (SEQ ID NO:1) (FIG. 1F), is only marginally effective as a cytoprotective agent at 50 μM. FIGS. 2A–2G shows that, at a concentration of 5 μM, Cbz-Val-Asp(OMe)-$CH_2F$ (FIG. 2D) still shows surprisingly strong cytoprotective action, while 5 μM BOC-Asp(OMe)-$CH_2F$ (FIG. 2C) and 5 μM Cbz-Glu(OMe)-Val-Asp(OMe)-$CH_2F$ (FIG. 2E) are less effective. The CPP32 inhibitor, Cbz-Asp(OMe)-Glu(OMe)-Val-Asp(OMe)-$CH_2F$ (SEQ ID NO:1) (FIG. 2F), has no cytoprotective properties at 5 μM. FIGS. 3A–3G shows that, even at 0.5 μM, Cbz-Val-Asp(OMe)-$CH_2F$ (FIG. 3D) is still an effective cytoprotectant, while the other compounds (FIGS. 3C, 3E and 3F) give slight or no cytoprotection. These experiments demonstrate that Cbz-Val-Asp(OMe)-$CH_2F$ can protect HeLa cells from TNF-α/CHX-induced apoptosis at concentrations 10 to 100 fold lower than other putative anti-apoptotic agents.

Figure 4:
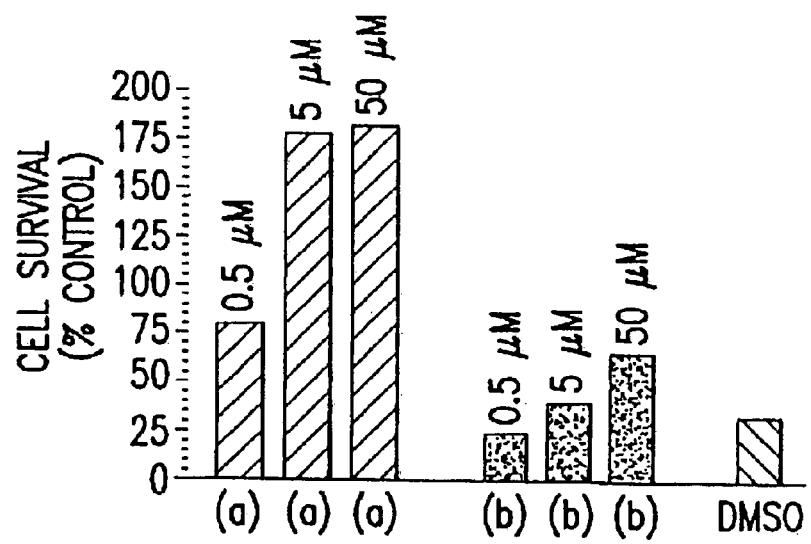
FIG. 4 depicts a bar graph showing the protection of HeLa cells from TNF-α/CHX with various concentrations of Cbz-Val-Asp(OMe)-$CH_2F$ (a) compared to Cbz-Asp(OMe)-Glu(OMe)-Val-Asp(OMe)-$CH_2F$ (SEQ ID NO:1) (b).
Figure 5:
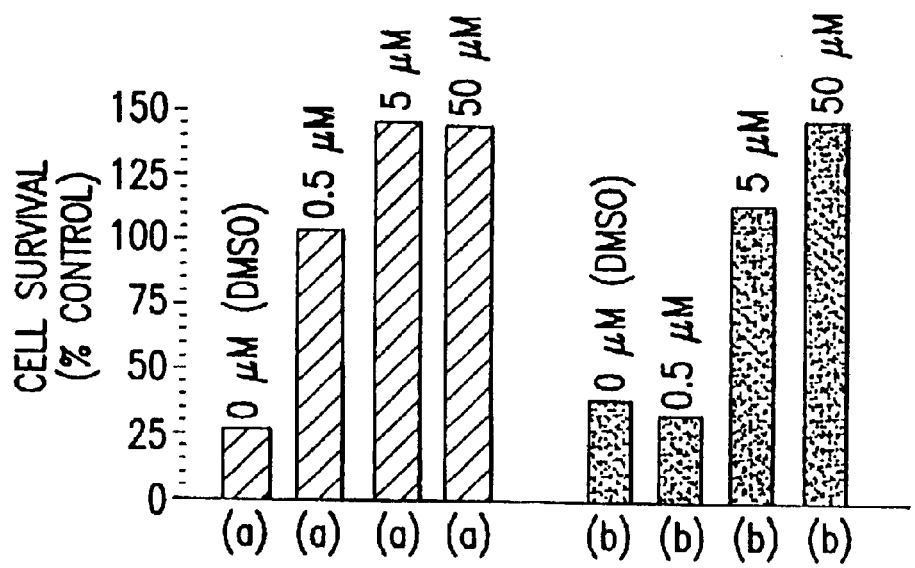
FIG. 5 depicts a bar graph showing the protection of HeLa cells from TNF-α/CHX with various concentrations of Cbz-Val-Asp(OMe)-$CH_2F$ (a) and BOC-Asp(OMe)-$CH_2F$ (b).

Quantitative experiments using calcein AM, as described above, corroborate the results obtained by microscopic examination. FIGS. 4 and 5 illustrate the results of two such experiments where the cytoprotective properties of Cbz-Val-Asp(OMe)-$CH_2F$ (a) were compared to BOC-Asp(OMe)-$CH_2F$ (b) (FIG. 5) and Cbz-Asp(OMe)-Glu(OMe)-Val-Asp(OMe)-$CH_2F$ (SEQ ID NO:1) (c) (FIG. 4) at three concentrations (0.5, 5 and 50 μM). FIG. 4 shows that Cbz-Asp(OMe)-Glu(OMe)-Val-Asp(OMe)-$CH_2F$ (SEQ ID NO:1) (b) is only minimally effective in protecting HeLa cells from TNF-α/CHX, even at the highest concentration used (50 μM). FIG. 5 shows that BOC-Asp(OMe)-$CH_2F$ (b) is an effective cytoprotectant at 50 and 5 μM, but its activity decreases dramatically at 0.5 μM. By contrast, Cbz-Val-Asp(OMe)-$CH_2F$ (a) is as effective a cytoprotectant at 0.5 μM as Cbz-Asp(OMe)-Glu(OMe)-Val-Asp(OMe)-$CH_2F$ (SEQ ID NO:1) (b) is at 50 μM (FIG. 4). Furthermore, 0.5 μM Cbz-Val-Asp(OMe)-$CH_2F$ (a) is highly active while 0.5 μM BOC-Asp(OMe)-$CH_2F$ (b) is inactive (FIG. 5).

Figure 6:
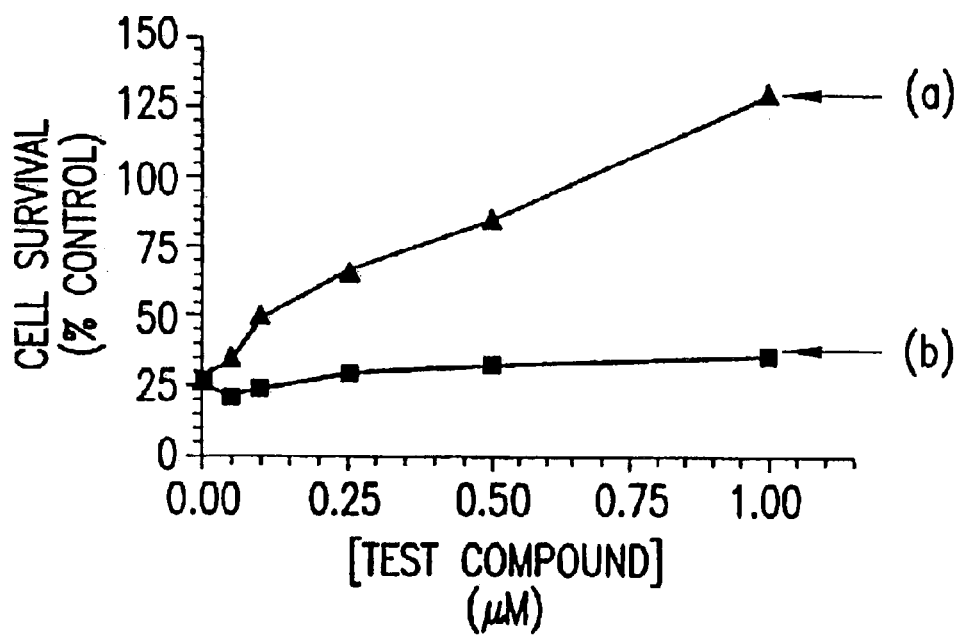
FIG. 6 depicts a graph showing the protection of HeLa cells from TNF-α/CHX with various low doses of Cbz-Val-Asp(OMe)-$CH_2F$ (a) compared to Cbz-Val-Ala-Asp(OMe)-$CH_2F$ (b).

In order to determine the effect of Cbz-Val-Asp(OMe)-$CH_2F$ at low doses, HeLa cells were treated with a range of concentrations from 0.05 μM to 1 μM. As shown in FIG. 6, Cbz-Val-Asp(OMe)-$CH_2F$ (a) gave significant protection at concentrations as low as 0.25 μM. By contrast, Cbz-Val-Ala-Asp(OMe)-$CH_2F$ (b), an anti-apoptotic agent widely used in cell death research, shows no cytoprotection in this concentration range.

Taken together, the experiments illustrated by FIGS. 1A through 6 show that Cbz-Val-Asp(OMe)-$CH_2F$ is a surprisingly potent anti-apoptotic agent in intact cells and is more potent than any other known caspase inhibitor.

EXAMPLE 22

Inhibition of PARP Cleavage in Jurkat Cells

The cleavage of the enzyme poly(ADP)ribose polymerase (PARP) appears to occur in all cells in which the caspase proteolytic cascade is activated. For this reason, PARP cleavage is widely used as a biochemical marker for caspase-mediated apoptosis. The ability of a cytoprotective drug to block PARP cleavage is considered to be an indication of the drug's ability to inhibit the caspase proteolytic cascade and, in particular, CPP32 (caspase-3), the main PARP protease. The ability of Cbz-Val-Asp(OMe)-$CH_2F$ to inhibit PARP cleavage was examined during Fas-mediated apoptosis of Jurkat cells, a human T-cell line. This cell culture model of apoptosis is well-characterized and is known to involve activation of at least two caspases, caspase-3 (CPP32) and caspase-8 (FLICE/MACH).

For PARP cleavage assays, Jurkat cells were seeded at a density of 500,000 cells per well in six-well multidishes in RPMI 1640 medium containing 10% FBS. The cells were pre-incubated with Cbz-Val-Asp(OMe)-$CH_2F$ or other test compounds for 2 hours at 37° C. in a $CO_2$ incubator and then a monoclonal antibody to Fas was added at a final concentration of 500 ng/mL. Incubation at 37° C. in a $CO_2$ incubator was continued for an additional 4 hours. At the end of the incubation period, the cells were harvested by centrifugation and lysed in a buffer containing 50 mM Tris-HCl, pH 7.4, 150 mM NaCl, 1% NP-40, 0.25% sodium deoxycholate, 1 mM EDTA and a cocktail of protease inhibitors. An amount of lysate corresponding to 10 to 20 μg of protein was loaded on a 7.5% SDS polyacrylamide gel and electrophoresed for 2 to 2.5 hrs at 25 mA. The protein was then transferred to a PVDF membrane, probed with a rabbit polyclonal antibody to PARP, and visualized using chemiluminescence.

Figures 7D, 7E:
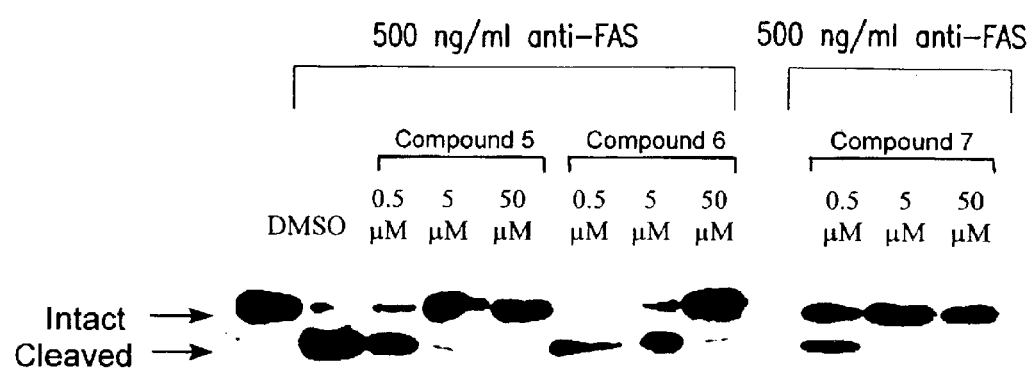

FIGS. 7A–7E shows the result of three such experiments. Jurkat cells were pre-incubated with 0.5, 5, or 50 μM of the following compounds: Cbz-Val-Asp(OMe)-$CH_2F$ (compound 1); BOC-Asp(OMe)-$CH_2F$ (compound 5); Cbz-Asp-α-([2,6-dichlorobenzoyloxy]-methyl ketone) (compound 6), Cbz-Glu(OMe)-Val-Asp(OMe)-$CH_2F$ (compound 3), Cbz-Asp(OMe)-Glu(OMe)-Val-Asp(OMe)-$CH_2F$ (SEQ ID NO:1) (compound 2), Cbz-Ile-Glu(OMe)-Thr-Asp(OMe)-$CH_2F$ (SEQ ID NO:2) (compound 4), or Cbz-Val-Ala-Asp(OMe)-$CH_2F$ (compound 7). The cells were then treated with antiFas and processed for Western Blotting. Cbz-Val-Asp(OMe)-$CH_2F$ (compound 1) completely inhibited PARP cleavage at 50 and 5 μM and afforded significant inhibition of cleavage even at 0.5 μM (FIG. 7A). By contrast, Cbz-Asp(OMe)-Glu(OMe)-Val-Asp(OMe)-$CH_2F$ (SEQ ID NO:1)(compound 2) (FIG. 7A) and Cbz-Ile-Glu(OMe)-Thr-Asp(OMe)-$CH_2F$ (SEQ ID NO:2) (compound 4) (FIG. 7C) and Cbz-Asp-DCB (compound 6) (FIG. 7D) inhibited PARP cleavage completely at 50 μM, but were only marginally effective inhibitors at 5 μM and 0.5 μM. BOC-Asp(OMe)-$CH_2F$ (compound 5) (FIG. 7D) and Cbz-Val-Ala-Asp(OMe)-$CH_2F$ (compound 7) (FIG. 7E) and Cbz-Glu(OMe)-Val-Asp(OMe)-$CH_2F$ (compound 3) (FIG. 7B) were effective inhibitors of PARP cleavage at concentrations of 50 and 5 μM, but were only marginally effective at 0.5 μM, a concentration at which Cbz-Val-Asp(OMe)-$CH_2F$ (compound 1) still showed significant inhibition (FIG. 7A). These experiments demonstrate that Cbz-Val-Asp(OMe)-$CH_2F$ can block the caspase proteolytic cascade in intact cells at a concentration at least 10-fold lower than other known caspase inhibitors.

EXAMPLE 23

Enzyme Activity

The activities of Cbz-Val-Asp(OMe)-$CH_2F$ and Cbz-Val-Asp-$CH_2F$ (free acid) as inhibitors of CPP32, ICE and cathepsin B were measured in a fluorometric enzyme assay. Recombinant CPP32 protein and ICE protein were prepared by expressing DNA clones encoding these enzymes in an insect host cell (sf9 cells) using baculovirus as the vector. See, Webb, N.R. et al., "Expression of proteins using recombinant Baculovirus," *Techniques* 2:173–188 (1990). Preparations of native cathepsin were acquired from a commercial source. Enzyme activity was measured using synthetic peptide substrates attached to a fluorogenic leaving group. Cleavage of the synthetic substrate by the enzyme results in a fluorescent signal which is read in a spectrofluorometer or in a fluorometric microtiter plate reader.

CPP32 activity was measured using the following buffer conditions: 100 mM HEPES pH 7.5, with 10% sucrose, 1% CHAPS, 5 mM glutathione, and 5 μM peptide substrate. The peptide substrate consisted of an oligomer with the sequence Asp-Glu-Val-Asp (SEQ ID NO:1) with the fluorogenic compound aminomethylcoumarin conjugated to the C-terminus. The assay for enzyme activity was typically carried out at 37° C. for 30 minutes.

Table I lists the $IC_{50}$ of Cbz-Val-Asp(OMe)-$CH_2F$ and Cbz-Val-Asp-$CH_2F$ (free acid) for CPP32 and other proteases.

TABLE I

Potency of Cbz-Val-Asp(OMe)—$CH_2F$ and Cbz-Val-Asp-$CH_2F$ (free acid) as Inhibitors of CPP32 and Other Proteases

| Enzyme | Cbz-Val-Asp(OMe)—$CH_2F$ $IC_{50}$ (μM) | Cbz-Val-Asp$CH_2F$ (free acid) $IC_{50}$ (μM) |
|---|---|---|
| CPP32 | 1.1 | 0.043 |
| ICE | 0.9 | 0.02 |
| Cathepsin B | 0.3 | >10 |
| Factor Xa | >100 | >100 |
| Thrombin | >100 | >100 |

The results shown in Table I show that compounds of the present invention are moderately potent inhibitors of CPP32 and ICE. It also shows that Cbz-Val-Asp-$CH_2F$ is a potent and selective inhibitor for CPP32 and ICE.

The inhibitory activity of Cbz-Val-Asp-$CH_2F$ in recombinant caspase 3, 6, 7 and 8 obtained from PharMington (a Becton division company, San Diego, Calif.) were measured using Ac-DEVD-AMC (SEQ ID NO:1). The amount of each enzyme per assay was as following: 1 ng caspase3, 15 ng caspase6, 2 ng caspase7 and 60 ng caspase8. The enzyme reaction was conducted in 96-well plate using a caspase buffer (20 mM PIPES, 100 mM NaCl, 10 mM DTT, 1 mM EDTA, 0.1% CHAPS and 10% sucrose, pH 7.2) and the reaction was initiated by adding 10 μM Ac-DEVD-AMC (SEQ ID NO:1) (purchased from Quality Controlled Biochemicals, Inc. Hopkinton, Mass.). Twelve concentrations of Cbz-Val-Asp-$CH_2F$ ranged from 30 μM to 10 μM were tested after incubation of the compound with recombinant caspases for 30 minutes at 37° C. The plate was read with a fluorescence plate reader (EG&G WALLAG, model-1420-002) using excitation filter at 355 nm/emission filter at 460 nm. The data was analyzed using GraphPrism software. The data is summarized in Table II.

TABLE II

Potency of Cbz-Val-Asp-$CH_2F$ as Inhibitor of caspases

| | Caspase-3 | Caspase-6 | Caspase-7 | Caspase-8 |
|---|---|---|---|---|
| $IC_{50}$ (nM) | 19.8 | 18.4 | 6.8 | 7.2 |

The results shown in Table II show that Cbz-Val-Asp-$CH_2F$ is a potent inhibitor of all the caspases tested.

Table III shows the caspase-3 activity of various dipeptide inhibitors. The results show that Z-Val-Asp-$CH_2F$ is the most potent caspase-3 inhibitor among the compounds tested.

TABLE III

Caspase-3 activity of the dipeptide inhibitors

| Name | Caspase-3 IC$_{50}$ ($\mu$M) |
| --- | --- |
| Z-L-Val-Asp-fmk | 0.04 |
| Z-L-Leu-Asp-fmk | 0.2 |
| Z-L-Ile-Asp-fmk | 0.07 |
| Z-L-Phe-Asp-fmk | 0.4 |
| Z-Gly-Asp-fmk | 1.9 |
| Z-L-Ala-Asp-fmk | 0.6 |
| Z--Ala-Asp-fmk | 3.5 |
| Ac-L-Val-Asp-fmk | 0.25 |
| Z-L-Glu-Asp-fmk | 14.2 |
| Z-L-Lys-Asp-fmk.TFA | 1.6 |
| Z-N-Me-L-Val-Asp-fmk | 1.3 |
| Z-L-Pro-Asp-fmk | 0.41 |
| Z-L-His-Asp-fmk | 0.77 |
| Z-L-Tyr-Asp-fmk | 0.66 |

EXAMPLE 24

Effect of Z-VD-fmk on PARP Cleavage

Poly(ADP)ribose polymerase (PARP) was one of the first caspase-3 substrates identified and the cleavage of PARP is still considered to be a near-universal marker for caspase-3 activation and caspase-mediated apoptosis. The ability of an anti-apoptotic compound to block PARP cleavage is therefore a useful indicator of its ability to inhibit apoptosis. The potency of Z-VD-fmk in a PARP cleavage assay was tested using antiFas-treated Jurkat cells. 2×10$^6$ Jurkat cells were seeded in each well of a 6-well dish and pre-incubated with test compounds for 30 minutes. The cells were then challenged with 500 ng/mL of an agonistic antiFas antibody or PBS for 4 hours. The cells were then harvested, pelleted gently, washed two times with PBS and lysed in RIPA buffer. Aliquots of the lysate were analyzed by SDS-PAGE and the proteins were transferred to PVDF membranes for Western blotting. The primary antibody was a polyclonal antiPARP serum which cross-reacts with both full-length PARP and the caspase-3-generated cleavage product.

Figure 8A:
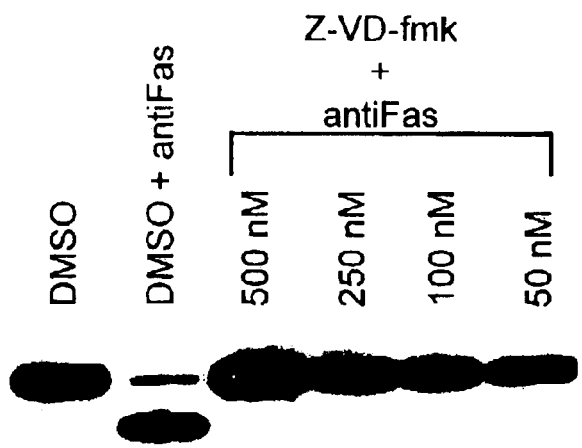
FIGS. 8A and 8B depict the photographs of PARP cleavage, showing inhibition of PARP cleavage in antiFas treated Jurkat cells by Z-VD-fmk and Z-VAD-fmk.
Figure 8B:
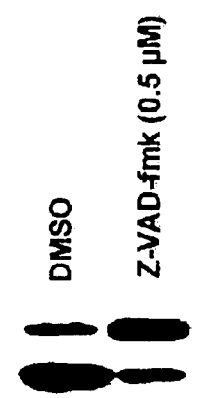

FIG. 8A shows that Z-VD-fmk completely inhibits PARP cleavage at concentrations of 500 and 250 nM (note absence of the 85 kDa band). Z-VD-fmk still retains much of its inhibitory activity even at concentrations as low as 50 nM (FIG. 8A). By contrast, Z-VAD-fmk, although an effective inhibitor of PARP cleavage at 5 $\mu$M (data not shown), is much less effective at 500 nM (FIG. 8B). These experiments show that Z-VD-fmk is at least 10-fold more potent as an inhibitor of PARP cleavage in intact cells than is Z-VAD-fink and Z-VD-fmk has an IC$_{50}$ value of less than 50 nM in this model of whole-cell apoptosis.

EXAMPLE 25

Effect of Z-VD-fmk on TNF-α-induced Cell Death

Tumor necrosis factor alpha (TNF-α) can trigger apoptosis in a number of cell types by initiating the caspase cascade and its apoptosis inducing activity can be inhibited by peptide-based caspase inhibitors. However, high concentrations of the inhibitors (50 $\mu$M or greater) is required to have good anti-apoptotic effect. HeLa cells, a cell line commonly employed in TNF-α cell death studies, was used here to determine the anti-apoptotic potency of Z-VD-fmk.

HeLa cells were seeded in 48-well multidishes at a density of 50,000 cells per well 24 hours before treatment. They were then pre-incubated with varying concentrations of Z-VD-fmk for 2 hours and challenged with TNF-α (25 ng/mL) and cycloheximide (CHX; 30 $\mu$g/mL). The cultures were incubated for an additional 24 hours and dead cells were removed by two washes with PBS. The density of surviving cells was then measured by incubating each culture for 45 minutes with calcein AM, a profluorescent dye which is taken up by living cells and converted to a fluorescent product. The resulting data were expressed as % control values (control values were cells incubated with cycloheximide but without TNF-α).

Figure 9:
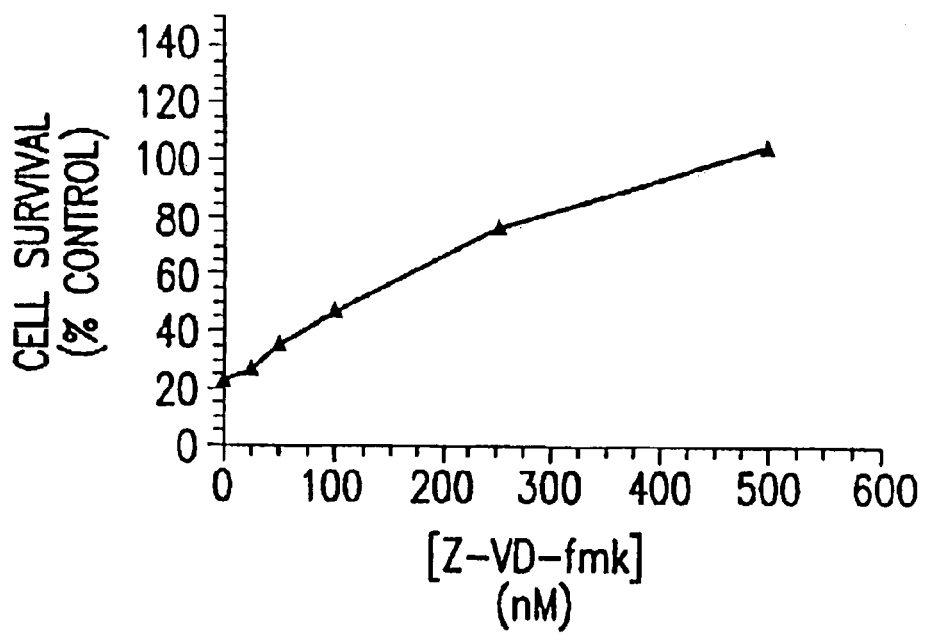
FIG. 9 depicts the graph of cell survival vs Z-VD-fmk concentration, showing inhibition of TNF-α-induced cell death by Z-VD-fmk.

FIG. 9 shows the results of Z-VD-fmk with tested concentrations ranging from zero to 500 nM. Z-VD-fmk provided good cytoprotection at concentrations approaching 100 nM. By contrast, Z-VAD-fmk loses much of its cytoprotective properties below 1 $\mu$M (data not shown). Tetrapeptide inhibitors, such as Z-DEVD-fmk (SEQ ID NO:1) and Ac-DEVD-CHO (SEQ ID NO:1), are very ineffective below 50 $\mu$M (data not shown). Therefore Z-VD-fmk not only inhibits PARP cleavage at sub-micromolar concentrations (see Example 24), but also inhibits cell death at sub-micromolar concentrations, and is much more effective than known tripeptide and tetrapeptide inhibitors.

EXAMPLE 26

Effect of Z-VD-fmk on DNA Laddering

In the later stages of apoptosis, cells begin to literally fall apart as pieces of the cytoplasm are shed (through blebbing) and the nucleus is disassembled. One of the hallmarks of nuclear disassembly is the cleavage of genomic DNA into nucleosome-sized fragments (termed "DNA laddering"). DNA laddering, like other late stage apoptotic events, is considered to be irreversible, so it is important to determine whether an anti-apoptotic drug can prevent its occurrence.

The ability of Z-VD-fmk to block DNA laddering was tested using antiFas-treated Jurkat cells. Jurkat cells were plated in 60 mm dishes at a density of 5×10$^6$ cells and pre-incubated with varying concentrations of Z-VD-fmk. They were then challenged with antiFas at 100 ng/mL for 4 hours, harvested, and pelleted and washed with PBS twice. Genomic DNA was isolated using the method of Eldadah et al. (1996). Briefly, the cells were lysed in 2 mL of 7M guanidine HCl and mixed with 1 mL of Wizard miniprep DNA purification resin (Promega). The resin/DNA complex was washed twice with buffer and the DNA was eluted in TE. 1 to 2 $\mu$g of this DNA sample was electrophoresed on a 1% agarose/TBE gel and the gel was stained with ethidium bromide.

Figure 10:
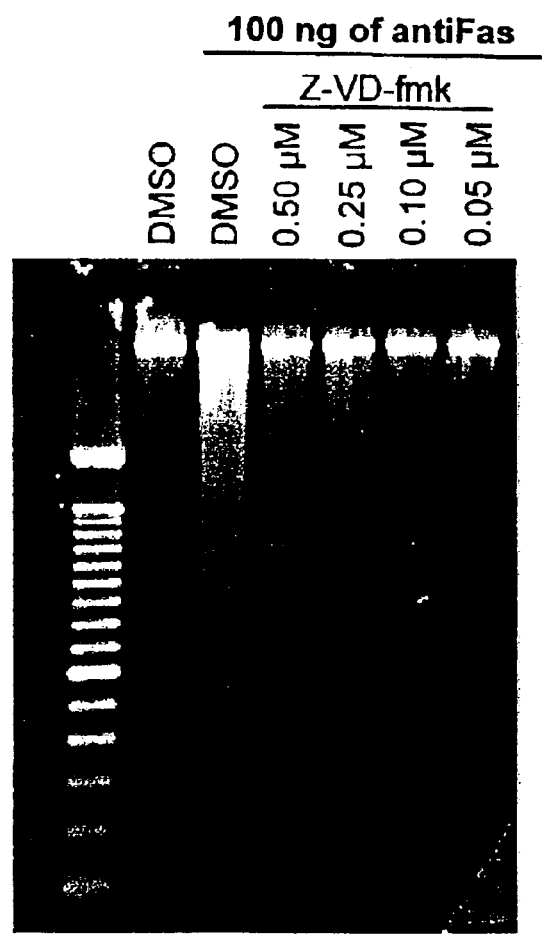
FIG. 10 depicts the photograph of DNA laddering, showing inhibition of DNA laddering in antiFas treated Jurkat cells by Z-VD-fmk.

FIG. 10 shows the results of a DNA laddering assay in which the cells were pre-incubated with Z-VD-fmk or drug vehicle (DMSO). Vehicle treated cells which were challenged with antiFas show a characteristic laddering pattern of DNA extending down to about 300 bp. By contrast, Z-VD-fmk inhibits ladder formation at a dose as low as that of 50 nM.

This result shows that Z-VD-fmk can block a critical late-stage apoptotic event (DNA laddering) at sub-micromolar concentrations comparable to those concentrations which block cell death and PARP cleavage. Based on this experiment and the data described in Examples 24 and 25, it is concluded that Z-VAD-fmk is a highly effective, sub-micromolar apoptotic inhibitor in whole-cell model of apoptosis.

EXAMPLE 27

Anti-apoptotic Activity of Cbz-Val-Asp-CH$_2$F in the Mouse Liver Apoptosis Model Three to four week old female mice were used in the studies. Liver degeneration was induced by intravenous injection with 2–6 μg of a purified hamster anti-mouse Fas monoclonal antibody (clone Jo2, Pharmingen) against mouse Fas antigen diluted in 80 μl of phosphate buffered physiological saline (Rodriguez, et al., 1996). Mortality was used as the end point to assess liver degeneration. Cbz-Val-Asp-$CH_2F$ was formulated in Tris buffer for intravenous infusion and tested at a dose of 1–10 mg/kg given IV via the tail vein. Ten minutes later, animals were injected with Fas antibody. Mortality was counted at 30 mins, 1, 3 and 24 h. For each compound there were groups of control animals that receive Fas antibody only. Those receiving the highest dose was observed for acute behavioral effects (e.g. sedation, locomoter activity, changes in gait, convulsions, straub tail, tremor etc.), and then housed overnight and checked the next day for toxicity/mortality.

In these experiments, Cbz-Val-Asp-$CH_2F$ was a surprisingly potent inhibitor of antiFas-induced lethality. A single 1 mg/kg IV dose completely protected mice from antiFas up to 1 h after antibody administration, and dose as low as 0.25 mg/kg was found to still give almost 100% protection. By contrast, in vehicle control groups all the mice were dead at this time-point. Cbz-Val-Asp-$CH_2F$ also showed substantial protection up to 24 h (28% survival). Separate studies showed that the protection against lethality was associated with the predicted attenuation in the induction of the liver enzymes SPGT and SGOT.

These data demonstrates that Cbz-Val-Asp-$CH_2F$ is highly active in vivo following systemic administration in the mouse liver apoptosis model.

EXAMPLE 28

Neuroprotection of Cbz-Val-Asp-$CH_2F$ in Rat Model of Focal Ischemia (i) Preparative Surgery: Male Fischer-344 rats (Harlan Sprague Dawley, Calif.) weighing 200–240 g, were used. Animals were initially anesthetized with 3% halothane in a mixture of 30% oxygen and 70% air. Halothane level were reduced to 1.5% for maintenance of anesthesia throughout surgery. Preparative surgery includes: (a) Intravenous catheter implantation: the left femoral vein were exposed and a Teleflex catheter, filled with vehicle, were inserted up to the inferior vena cava, for subsequent drug administration. (b) Arterial catheter implantation: the femoral artery were cannulated to allow monitoring of the blood pressure, and other physiological conditions include $pO_2$, $pCO_2$, pH, glucose, hematocrite, during ischemia, initial drug administration, and the time of arterial reperfusion. Both arterial and venous catheters were exteriorized through the back of the animal, to allow free movement. (c) A PhysioTel Transmitter (Data Sciences International, Mich.) were implanted into the peritoneal cavity to remotely monitor the body temperature of the animals for 22 hours.

(ii) Physiological parameters: Core body temperature was maintained at 37.5° C. during surgery, using a YSI Reusable Temperature Probe (YSI Co. Inc., Yellow Spring, Ohio) connected to a YSI Temperature Control Unit (Model 73A, YSI Co. Inc., Ohio) and a Electric Heating Pad (Model 756, Sunbean-Oster Co. Inc., Hattiesburg, Miss.). Following ischemia, the PhysioTel Transmitter was activated and core body temperature was recorded every 5 minutes. Systemic blood pressure was monitored throughout surgery, during intravenous drug infusion (bolus), and 1, 2, 3, and 4 hours after the onset of ischemia. Other physiological conditions, including $pO_2$, $pCO_2$, pH, glucose, and hematocrite were examined at the time of arterial occlusion and reperfusion.

(iii) Transient focal ischemia model: Following preparative surgery, a ventral midline cervical incision was made to expose both CCAs. The right CCA was permanently ligated with 4-o silk ligature, while the left CCA was clamped with an atraumatic aneurysm clip. A 1-cm incision perpendicular to and bisecting a line between the lateral canthus of the right eye and the external auditory canal was made. The underlying temporalis muscle was excised and retracted and under direct visualization with the aid of a dissecting microscope (Model SZ-STB1, Olympus, Japan), the middle cerebral artery (MCA) was exposed through a 2 mm burr hole drilled 2–3 mm rostral to the fusion of the zygomatic arch and the squamosal bone. Drilling was done under a continuous irrigation of physiological saline. The dura was cut and retracted to expose the MCA in the rhinal fissure. A Codman micro-aneurysm clip (No. 1) was used to temporarily occlude the MCA as it crosses the rhinal fissure. Flow interruption was verified with dissecting microscopic. Incisions were closed with surgical clips, anesthesia was discontinued, and the animals were returned to their cages after waking up (within minutes). Rats subject to transient ischemia weree reanesthetized after a 2.5 hours after MCA occlusion. After verification of MCA occlusion, the clips on the MCA and left CCA were removed and restoration of blood flow in the MCA confirmed visually. The incision was closed, and rats were returned to their cages. Animals requiring short term recovery were allowed to survive for 24 hours. All animals were deeply anesthetized prior to sacrifice. Brains was removed, and 2 mm coronal sections were sliced and placed in TTC. Infarcted tissue appeared pale, and distinguishable from adjacent viable tissue. The areas of cortical and subcortical infarction were measured blindly with imaging processing software, and the volume of infarction was calculated by adding up individual measures with known thickness.

(iv) Statistical Analysis: All physiological parameters, temperature recordings, and the volumes of cortical infarction were compared statistically among experimental and control groups, for each sub-set of animals. Statistical analyses were conducted using Sigmastat software (Jandel Scientific Software, San Rafael, Calif.). Student's t tests were used for unpaired data and ANOVA for multiple comparisons. A p value of <0.05 was considered significant. Graphs were prepared on SigmaPlot v 2.01 software (Jandel Scientific).

The in vivo neuroprotective properties of Cbz-Val-Asp-$CH_2F$ were tested in two stroke studies in the rat (Fischer-344) transient focal ischemia model. Cbz-Val-Asp-$CH_2F$ was given as a 20 mg/kg IV bolus 10 minutes after the onset of ischemia, followed by a continuous IV infusion of 5 mg/kg/hr. In Experiment 1, the continuous infusion was given for 6 h. In Experiment 2, the infusion was extended to 12 h.

Figure 11A:
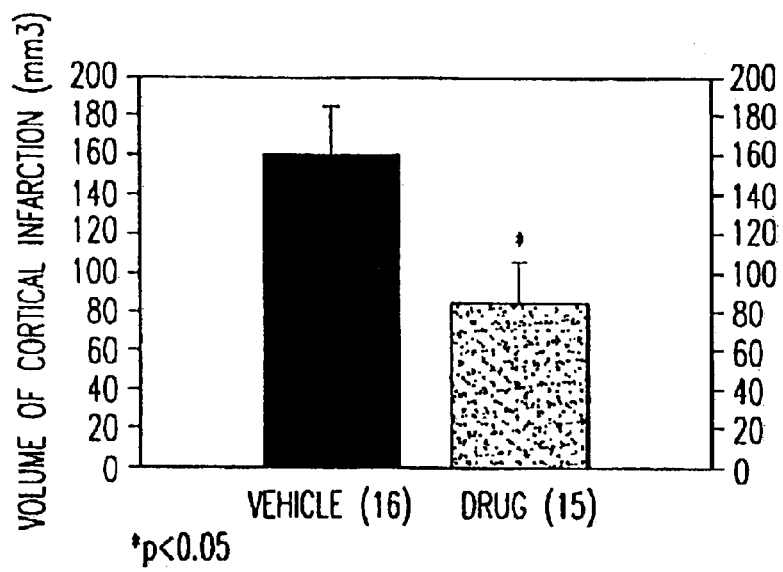
FIGS. 11A and 11B show the neuroprotective effects of systemically administered Cbz-Val-Asp-CH$_2$F in a rat transient focal ischemia model. Volume of cortical infarction was quantified following 2.25 h of transient focal ischmia and 22 h of reperfusion.
Figure 11B:
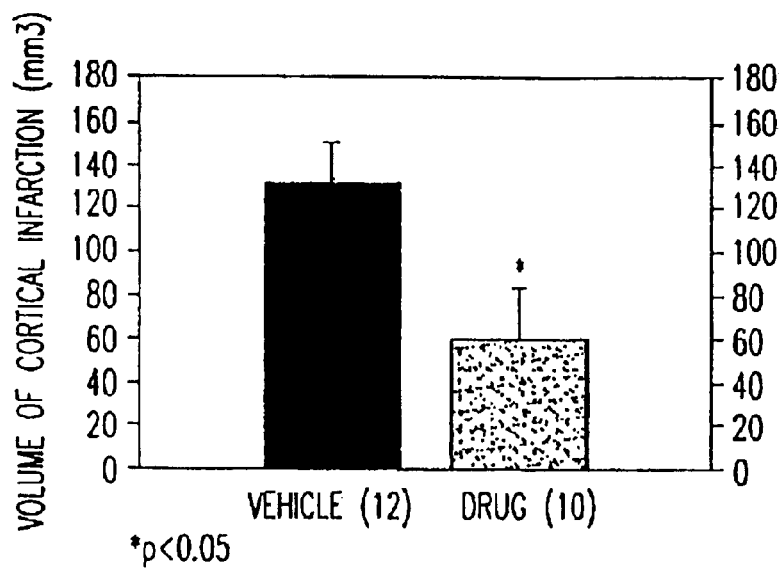

Cbz-Val-Asp-$CH_2F$ was found to significantly reduce cortical infarction in both studies: 46% (p<0.05) in Experiment 1 and 57% (p<0.05) in Experiment 2 (FIGS. 11A and 11B). There were no changes in blood pressure, blood gas, or temperature following drug administration. These results demonstrated that Cbz-Val-Asp-$CH_2F$ is well tolerated following acute IV dosing and is a potent neuroprotectant in a rat model of transient focal cerebral ischemia.

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A method of reducing or preventing cell death in a donor organ or tissue after it has been transplanted into a host due to the effects of host immune cells, comprising administering to said host in need thereof an effective amount of a compound of Formula I:

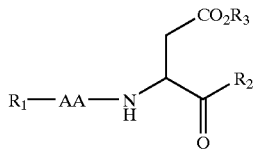

or a pharmaceutically acceptable salt or prodrug thereof, wherein:
  AA is a residue of an amino acid selected from the group consisting of valine (Val), isoleucine (Ile), and leucine (Leu);
  $R_1$ is an N-terminal protecting group selected from the group consisting of Cbz, Ac and Boc;
  $R_2$ is H or $CH_2R_4$, where $R_4$ is an electronegative leaving group; and
  $R_3$ is alkyl or H.

2. The method of claim 1, wherein $R_3$ is methyl or H.

3. The method of claim 1, wherein said compound is Cbz-Val-Asp-$CH_2$F or a pharmaceutically acceptable salt thereof.

4. The method of claim 1, wherein said compound is Cbz-Leu-Asp-$CH_2$F or a pharmaceutically acceptable salt thereof.

5. The method of claim 1, wherein said compound is Cbz-Ile-Asp-$CH_2$F or a pharmaceutically acceptable salt thereof.

6. The method of claim 1, wherein said compound is Ac-Val-Asp-$CH_2$F or a pharmaceutically acceptable salt thereof.

7. The method of claim 1, wherein said compound is Ac-Leu-Asp-$CH_2$F or a pharmaceutically acceptable salt thereof.

8. The method of claim 1, wherein said compound is Ac-Ile-Asp-$CH_2$F or a pharmaceutically acceptable salt thereof.

9. The method of claim 1, wherein said compound is Boc-Val-Asp-$CH_2$F or a pharmaceutically acceptable salt thereof.

10. The method of claim 1, wherein said compound is Boc-Leu-Asp-$CH_2$F or a pharmaceutically acceptable salt thereof.

11. The method of claim 1, wherein said compound is Boc-Ile-Asp-$CH_2$F or a pharmaceutically acceptable salt thereof.

12. The method of claim 1, wherein said compound is Cbz-Val-Asp(OMe)-$CH_2$F or a pharmaceutically acceptable salt thereof.

13. The method of claim 1, wherein said compound is Cbz-Leu-Asp(OMe)-$CH_2$F or a pharmaceutically acceptable salt thereof.

14. The method of claim 1, wherein said compound is Cbz-Ile-Asp(OMe)-$CH_2$F or a pharmaceutically acceptable salt thereof.

* * * * *

SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Asp Glu Val Asp
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide

<400> SEQUENCE: 2

Ile Glu Thr Asp
1